(12) United States Patent
Malesky et al.

(10) Patent No.: US 10,640,959 B2
(45) Date of Patent: May 5, 2020

(54) URINAL SCREENS AND ASSEMBLIES

(71) Applicant: GPCP IP HOLDINGS LLC, Atlanta, GA (US)

(72) Inventors: Jacob Edward Malesky, Menasha, WI (US); Eric Paul Peterson, Mount Horeb, WI (US); Jeffrey Charles Duhacek, Neenah, WI (US)

(73) Assignee: GPCP IP Holdings LLC, Atlanta, GA (US)

( * ) Notice: Subject to any disclaimer, the term of this patent is extended or adjusted under 35 U.S.C. 154(b) by 0 days.

(21) Appl. No.: 16/000,479

(22) Filed: Jun. 5, 2018

(65) Prior Publication Data

US 2018/0347161 A1 Dec. 6, 2018

Related U.S. Application Data

(60) Provisional application No. 62/516,078, filed on Jun. 6, 2017.

(51) Int. Cl.
| | |
|---|---|
| *E03C 1/26* | (2006.01) |
| *E03C 1/264* | (2006.01) |
| *E03D 13/00* | (2006.01) |
| *E03D 9/00* | (2006.01) |
| *A61L 9/05* | (2006.01) |
| *A61L 9/04* | (2006.01) |

(Continued)

(52) U.S. Cl.
CPC .............. *E03C 1/264* (2013.01); *A61L 9/042* (2013.01); *A61L 9/05* (2013.01); *E03D 9/007* (2013.01); *E03D 9/02* (2013.01); *E03D 13/005* (2013.01); *A61L 9/01* (2013.01); *A61L 9/12* (2013.01); *E03D 2009/024* (2013.01)

(58) Field of Classification Search
CPC ... E03C 1/282; E03C 1/126; E03D 2009/024; E03D 13/005; E03D 9/02; E03D 9/022
USPC .......................................................... 4/300.3
See application file for complete search history.

(56) References Cited

U.S. PATENT DOCUMENTS

| 571,275 A | 11/1896 | Maxwell et al. |
|---|---|---|
| 647,895 A | 4/1900 | Burson |

(Continued)

FOREIGN PATENT DOCUMENTS

| AU | 636863 B | 6/1991 |
|---|---|---|
| AU | 2015100064 A1 | 2/2015 |

(Continued)

OTHER PUBLICATIONS

International Search Report and Written Opinion for International Application No. PCT/US2018/036070 dated Jul. 27, 2018 (12 pages).

(Continued)

*Primary Examiner* — Janie M Loeppke
(74) *Attorney, Agent, or Firm* — Eversheds Sutherland (US) LLP

(57) ABSTRACT

Urinal screens are provided including an outer ring and a web portion bounded by the outer ring and formed from a plurality of web strings disposed in a mesh pattern, such that a plurality of open areas are defined among the web strings. The web portion includes a vaulted portion. Urinal screen assemblies are also provided and include a urinal screen and a bioenzymatic block containing odor combatting chemistry disposed in a void formed by the vaulted portion of the urinal screen.

22 Claims, 13 Drawing Sheets

(51) Int. Cl.
  *E03D 9/02* (2006.01)
  *A61L 9/01* (2006.01)
  *A61L 9/12* (2006.01)

(56) References Cited

U.S. PATENT DOCUMENTS

| | | |
|---|---|---|
| 675,947 A | 6/1901 | Hach |
| 683,419 A | 9/1901 | Burson |
| 927,026 A | 7/1909 | Clayton |
| 1,186,345 A | 6/1916 | Sleight |
| 1,430,598 A | 10/1922 | Sleight |
| 2,046,214 A | 6/1936 | Selig |
| 2,211,970 A | 8/1940 | Fischer |
| 2,718,013 A | 9/1955 | Rajnicek |
| 2,813,631 A | 11/1957 | Odman |
| 2,974,324 A | 3/1961 | Lundelius |
| D194,776 S | 3/1963 | Clark |
| D194,777 S | 3/1963 | Clark |
| 3,170,169 A | 2/1965 | Clark |
| 3,248,740 A * | 5/1966 | Wisnom .................. E03D 13/00 4/222.1 |
| 3,597,772 A | 8/1971 | Leavitt |
| 3,760,429 A | 9/1973 | Brownstein |
| 3,994,439 A | 11/1976 | Van Breen et al. |
| 4,044,405 A | 8/1977 | Kreiss |
| 4,095,031 A | 6/1978 | Engle |
| 4,103,367 A | 8/1978 | Kaufer |
| 4,135,261 A | 1/1979 | Uhrman |
| D253,145 S | 10/1979 | Adam |
| D253,146 S | 10/1979 | Adam |
| D255,744 S | 7/1980 | Dekko |
| 4,215,443 A | 8/1980 | Babik |
| D258,181 S | 2/1981 | Adam |
| D258,472 S | 3/1981 | Adam |
| D259,225 S | 5/1981 | Scheer |
| 4,492,644 A | 1/1985 | Matsumoto et al. |
| 4,552,692 A | 11/1985 | Gillespie |
| 4,574,400 A | 3/1986 | Annowksy |
| 4,574,403 A | 3/1986 | Dintemann et al. |
| 4,671,976 A | 6/1987 | Vidal |
| 4,761,437 A | 8/1988 | Christie |
| 5,019,346 A | 5/1991 | Richter et al. |
| D329,893 S | 9/1992 | Luedtke et al. |
| 5,165,119 A | 11/1992 | Yamato |
| D332,302 S | 1/1993 | Brown |
| D336,948 S | 6/1993 | Frankel |
| 5,312,624 A | 5/1994 | Richter et al. |
| 5,313,672 A | 5/1994 | Luedtke et al. |
| 5,336,424 A | 8/1994 | Van Vlahakis et al. |
| 5,365,616 A | 11/1994 | Morad |
| D353,445 S | 12/1994 | Morad |
| 5,379,917 A | 1/1995 | Brown et al. |
| D355,807 S | 2/1995 | O'Rourke |
| 5,398,347 A | 3/1995 | Luedtke et al. |
| 5,489,415 A | 2/1996 | Val Vlahakis et al. |
| D370,938 S | 6/1996 | Roach |
| 5,567,389 A | 10/1996 | Birbara et al. |
| 5,595,324 A | 1/1997 | Brown et al. |
| 5,604,937 A | 2/1997 | Davenport |
| D393,896 S | 4/1998 | Wagner et al. |
| 5,774,905 A * | 7/1998 | Wager .................. E03D 13/005 4/222.1 |
| 5,799,826 A | 9/1998 | Brown et al. |
| 5,809,590 A | 9/1998 | Williams et al. |
| 5,813,058 A | 9/1998 | Quigley et al. |
| D410,281 S | 5/1999 | Walker |
| 6,055,681 A | 5/2000 | Lyons |
| 6,062,425 A | 5/2000 | Brown et al. |
| D427,295 S | 6/2000 | Wagner |
| D428,120 S | 7/2000 | Zaldivar |
| 6,081,937 A | 7/2000 | Whitacre |
| 6,197,321 B1 | 3/2001 | Richter et al. |
| 6,269,490 B1 | 8/2001 | Suski et al. |
| D456,492 S | 4/2002 | Lourens |
| D464,122 S | 10/2002 | Mangan |
| D479,313 S | 9/2003 | Navarra |
| 6,631,852 B1 | 10/2003 | O'Leary |
| 6,640,350 B1 | 11/2003 | Deutsch |
| D486,341 S | 2/2004 | Ruhl |
| 6,698,035 B1 | 3/2004 | Grueser |
| 6,729,506 B2 | 5/2004 | Brown et al. |
| 6,769,631 B2 | 8/2004 | Brown |
| 6,823,533 B2 | 11/2004 | Casari |
| 6,920,648 B1 | 7/2005 | Suski et al. |
| D520,610 S | 5/2006 | Wrate |
| 7,100,801 B2 | 9/2006 | Brown et al. |
| D530,215 S | 10/2006 | Brown et al. |
| 7,202,201 B1 | 4/2007 | Williams |
| D550,819 S | 9/2007 | Seehoff |
| D552,308 S | 10/2007 | Farr |
| 7,325,694 B2 | 2/2008 | Bushey |
| D564,550 S | 3/2008 | Pinchot |
| D564,551 S | 3/2008 | Pinchot |
| D565,067 S | 3/2008 | Pinchot |
| D565,610 S | 4/2008 | Pinchot |
| D565,611 S | 4/2008 | Pinchot |
| D565,612 S | 4/2008 | Pinchot |
| D565,613 S | 4/2008 | Pinchot |
| D565,614 S | 4/2008 | Pinchot |
| D565,615 S | 4/2008 | Pinchot |
| D566,145 S | 4/2008 | Pinchot |
| D568,349 S | 5/2008 | Pinchot |
| D571,898 S | 6/2008 | Gilligan |
| 7,398,565 B1 | 7/2008 | Chou |
| 7,410,513 B2 | 8/2008 | Requejo et al. |
| D577,416 S | 9/2008 | Buttgen |
| 7,461,413 B2 | 12/2008 | Lewis et al. |
| D584,863 S | 1/2009 | Garry |
| 7,484,675 B2 | 2/2009 | Brown |
| 7,597,949 B2 | 10/2009 | Wright |
| 7,618,532 B2 | 11/2009 | Worth |
| D612,914 S | 3/2010 | Morad |
| 7,735,694 B2 | 6/2010 | Brown et al. |
| D625,540 S | 10/2010 | Dukes |
| D629,636 S | 12/2010 | Wright |
| D629,875 S | 12/2010 | Sears |
| D630,306 S | 1/2011 | Seeholff et al. |
| D630,714 S | 1/2011 | Dukes |
| D631,531 S | 1/2011 | Morad |
| 7,887,697 B2 | 2/2011 | Worth |
| D639,410 S | 6/2011 | Ramirez |
| D642,003 S | 7/2011 | Wright |
| 8,007,707 B1 | 8/2011 | Brown et al. |
| 8,043,606 B2 | 10/2011 | MacBeth et al. |
| D655,793 S | 3/2012 | Emr |
| 8,127,969 B2 | 3/2012 | Brown et al. |
| D662,573 S | 6/2012 | Rogalski |
| D664,571 S | 7/2012 | Beyer |
| D678,482 S | 3/2013 | Williams |
| D678,483 S | 3/2013 | Barker |
| 8,409,433 B2 * | 4/2013 | Worth ...................... C02F 1/68 210/163 |
| D686,255 S | 7/2013 | Fu |
| D687,471 S | 8/2013 | Fu |
| D699,819 S | 2/2014 | Tung |
| 8,856,977 B2 | 10/2014 | Ramirez |
| D718,844 S | 12/2014 | Johansen |
| D718,845 S | 12/2014 | Johansen |
| 8,916,140 B2 | 12/2014 | MacBeath et al. |
| D724,702 S | 3/2015 | D'Amico |
| 8,974,736 B2 | 3/2015 | Brown et al. |
| D726,886 S | 4/2015 | Sutherland |
| D730,493 S | 5/2015 | Sehl |
| 9,027,172 B2 | 5/2015 | Fima |
| D743,509 S | 11/2015 | Traub et al. |
| D746,955 S | 1/2016 | Corder |
| 9,243,394 B2 | 1/2016 | Brown et al. |
| D754,829 S | 4/2016 | Krombein |
| 9,303,396 B1 | 4/2016 | Pemici et al. |
| 9,309,658 B1 | 4/2016 | Pemici et al. |
| 9,334,641 B2 | 5/2016 | Kobal |
| D759,791 S | 6/2016 | Hull |
| D759,792 S | 6/2016 | Flury |
| D778,411 S | 2/2017 | Brown et al. |

(56) References Cited

U.S. PATENT DOCUMENTS

| | | | |
|---|---|---|---|
| D778,412 S | 2/2017 | Brown et al. | |
| D790,042 S | 6/2017 | Ramirez | |
| D805,613 S | 12/2017 | D'Amico | |
| D824,495 S | 7/2018 | D'Amico et al. | |
| D824,496 S | 7/2018 | D'Amico et al. | |
| 10,066,382 B2 | 9/2018 | Muderlak et al. | |
| 2004/0034909 A1 | 2/2004 | Grueser | |
| 2004/0194198 A1 | 10/2004 | Casari | |
| 2006/0037128 A1 | 2/2006 | Lewis et al. | |
| 2006/0260032 A1 | 11/2006 | Smartt | |
| 2007/0023539 A1 | 2/2007 | Brown | |
| 2007/0044221 A1 | 3/2007 | Wise, Sr. | |
| 2007/0186337 A1 | 8/2007 | Emr | |
| 2007/0262006 A1 | 11/2007 | Worth | |
| 2007/0266486 A1 | 11/2007 | Ramirez | |
| 2008/0098505 A1 | 5/2008 | Casari | |
| 2008/0280095 A1 | 11/2008 | Wright | |
| 2008/0292855 A1 | 11/2008 | Manderfield et al. | |
| 2009/0026285 A1 | 1/2009 | Worth | |
| 2010/0183694 A1 | 7/2010 | Burke et al. | |
| 2010/0199412 A1 | 8/2010 | McAlpine | |
| 2010/0257664 A1 | 10/2010 | Kener | |
| 2011/0123761 A1 | 5/2011 | Wright | |
| 2011/0289665 A1 | 12/2011 | Lees | |
| 2011/0296597 A1 | 12/2011 | Brown et al. | |
| 2012/0137419 A1 | 6/2012 | Hofeling et al. | |
| 2013/0031708 A1 | 2/2013 | Sensel | |
| 2013/0067651 A1 | 3/2013 | Brown et al. | |
| 2013/0298840 A1 | 11/2013 | Mishan | |
| 2014/0007336 A1 | 1/2014 | Mills et al. | |
| 2014/0068848 A1 | 3/2014 | Neo | |
| 2014/0075663 A1 | 3/2014 | Irwin et al. | |
| 2014/0076358 A1 | 3/2014 | Irwin et al. | |
| 2014/0076983 A1 | 3/2014 | Irwin et al. | |
| 2014/0076984 A1 | 3/2014 | Irwin et al. | |
| 2014/0076991 A1 | 3/2014 | Irwin et al. | |
| 2014/0157501 A1 | 6/2014 | D'Amico | |
| 2014/0165277 A1 | 6/2014 | Schmed et al. | |
| 2014/0250577 A1 | 9/2014 | Nakamura et al. | |
| 2014/0259344 A1* | 9/2014 | Muderlak | E03D 13/005 4/256.1 |
| 2015/0013780 A1 | 1/2015 | Watkins | |
| 2015/0047114 A1 | 2/2015 | Ramirez | |
| 2015/0225937 A1 | 8/2015 | Brown et al. | |
| 2016/0102451 A1 | 5/2016 | Brown et al. | |
| 2016/0122992 A1 | 5/2016 | Brown et al. | |
| 2016/0215490 A1 | 7/2016 | Keune | |
| 2016/0222642 A1 | 8/2016 | Delaney | |
| 2016/0305107 A1 | 10/2016 | Muderlak et al. | |
| 2017/0067243 A1 | 3/2017 | Valencia et al. | |
| 2017/0096808 A1 | 4/2017 | D'Amico et al. | |
| 2018/0119403 A1 | 5/2018 | Crevier | |
| 2018/0305916 A1 | 10/2018 | Crevier | |

FOREIGN PATENT DOCUMENTS

| | | |
|---|---|---|
| CA | 1193199 A1 | 9/1985 |
| CN | 206346295 | 7/2017 |
| DE | 19832716 A1 | 1/2000 |
| DE | 102013108149 A1 | 2/2015 |
| GB | 2473055 A | 3/2011 |
| WO | 1994/020407 A1 | 9/1994 |
| WO | 1997/011234 A1 | 3/1997 |
| WO | 02/020172 A1 | 3/2002 |
| WO | 2004/055768 A1 | 7/2004 |
| WO | 2008/006234 A1 | 1/2008 |
| WO | 2008/089497 A1 | 7/2008 |
| WO | 2010/091862 A1 | 8/2010 |
| WO | 2014/043425 A3 | 3/2014 |
| WO | 2014/043725 A1 | 3/2014 |
| WO | 2014/093593 A1 | 6/2014 |
| WO | 2014/200400 A1 | 12/2014 |
| WO | 2015/088303 A1 | 6/2015 |
| WO | 2015/123223 A1 | 8/2015 |
| WO | 2016/060998 A1 | 4/2016 |
| WO | 2016/144153 A1 | 9/2016 |
| ZA | 200105073 A | 1/2002 |

OTHER PUBLICATIONS

Dustbane Catalogue, "3-D Shield", Copyright 2016, retrieved from http://dustbane.ca/product_sheet/en/3D_Shield_en_sm.pdf, on Oct. 3, 2016, 1 page.

HYSO HYScent Cyclone Urinal Screen—Ocean, retrieved from <https://cleaningsupply.com/catalog/p/523687EACH/HYSO-HYScent-Cyclone-Urinal-Screen-Ocean/>, on Jan. 17, 2017, 1 page.

Fresh Products, "Wave Deodorant Screen," Aug. 29, 2014 to May 26, 2015, Internet Archive <http://web.archive.org/web/*http://freshproducts.com/wave-deodrant-screen.html>, 4 pages.

Fresh Products, "Wave 2.0", Apr. 6, 2014 to Jan. 3, 2016, Internet Archive <http://web.archive.org/web/*http://freshproducts.com/wave-2-0.html>, 4 pages.

Impact, "Z-Screen™ Deodorizing Urinal Screens", May 2, 2014 to May 4, 2015, Internet Archive <http://web.archive.org/web/*http://catalog.impact-products.com/viewitems/urinal-screens/zk-screen%E2%84%A2-deodorizing-urinal-screens>, 2 pages.

Fresh Products, 2016 Catalog, retrieved from <http://freshproducts.com/media/wysiwyg/Literature/Fresh_Products_2016_Catalog_102915.pdf> on Jan. 26, 2016.

Hospeco, "Airworks Urinal Screens", 2 pages, retrieved from <https://www.hospeco.com/Products/AirWorks® %20Urinal%20Screens>, on Jan. 26, 2016.

Fresh Products, "Dome Urinal Screen (formerly known as RemindAir)", 2 pages, retrieved from <http://freshproducts,.com/dome-urinal-screen_html>, on Jan. 26, 2016.

Fresh Products, "Eco Bowl Clip 2.0", Mar. 27, 2014 to Jan. 16, 2016, Internet Archive <http://web.archive.org/web.archive.org/web/20160116002414/http://freshproducts.com/eco-bowl-clip.html>, 2 pages.

Hospeco, "Health Gards® Urinal Screen With Non-Para Block", 6 pages, retrieved from <https://www.hospeco.com/product/019>, on Jan. 26, 2016.

EKCOS, "ëkcoscreen", Nov. 16, 2010 to Jan. 11, 2016, Internet Archive <http://web.archive.org/web/20101116091823/http://www.wkcos.com/>, 1 page.

Rochester Midland Corporation, "Sanor Breeze Screen", Oct. 19, 2014 to Oct. 19, 2014, Internet Archive <http://web.archive.org/web/20141019152331/http://www.rochestermidland.com/products/personal_care/get_specs.cfm?PRODUCT_CODE=25190487>, 1 page.

Big D Industries, Inc., "The Pearl 3D (brochure)", 1 page, retrieved from <http://bigdind.com/product.aspx?id=BigD118>, on Jan. 26, 2016.

Fesh Products, "Toilet and Urinal—Fresh Products, Keeping Your World Smelling Fresh", retrieved from <http:/freshproducts.com/our-products/toilet-urinal>, on Oct. 6, 2015, 2 pages.

Fresh Products, "Wave 3D", May 1, 2015 to Jan. 16, 2016, Internet Archive <http://web.archive.org/web/20160116045345/http://freshproducts.com/wave-3d.html>, 3 pages.

Vectair Systems, Inc>, "Vectair V-Screen (brochure)", 2015, 2 pages, retrieved from <http://www.vectairsystems.com/products/washroom/v-screen-urinal-screens/>, on Jan. 26, 2016.

Ekcos, "Ekcos 30-Day Anti-Splash Protection", Copyright 2015, retrieved from <http://ekcos.com/restrooms_antisplash.html> on Mar. 3, 2016, 11 pages.

U.S. Appl. No. 29/541,529, Georgia-Pacific Consumer Products.
U.S. Appl. No. 29/578,140, Georgia-Pacific Consumer Products.
U.S. Appl. No. 29/578,135, Georgia-Pacific Consumer Products.
U.S. Appl. No. 29/553,957, Georgia-Pacific Consumer Products.
U.S. Appl. No. 15/285,951, Georgia-Pacific Consumer Products.

* cited by examiner

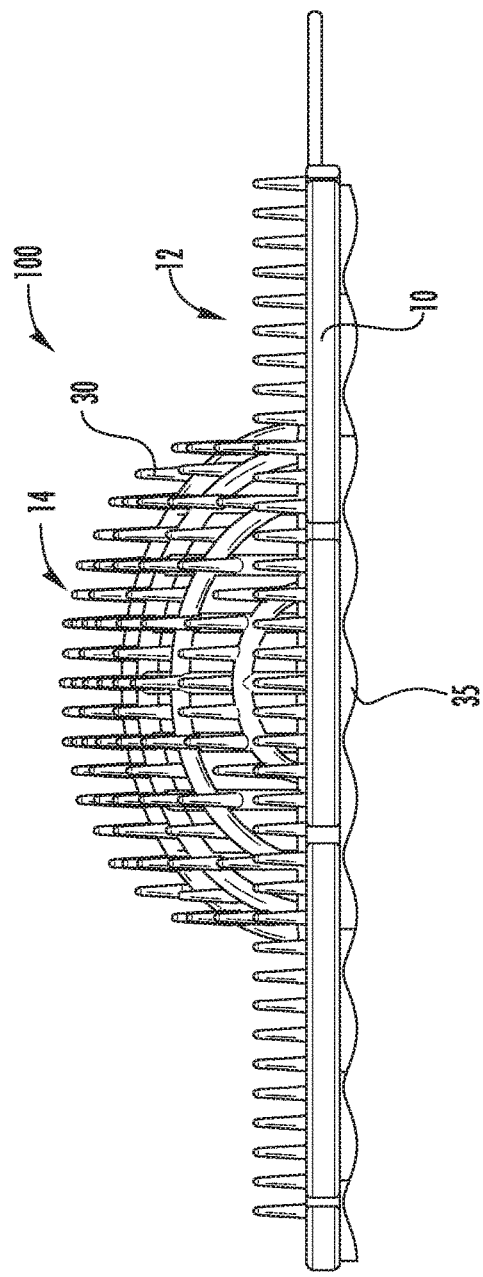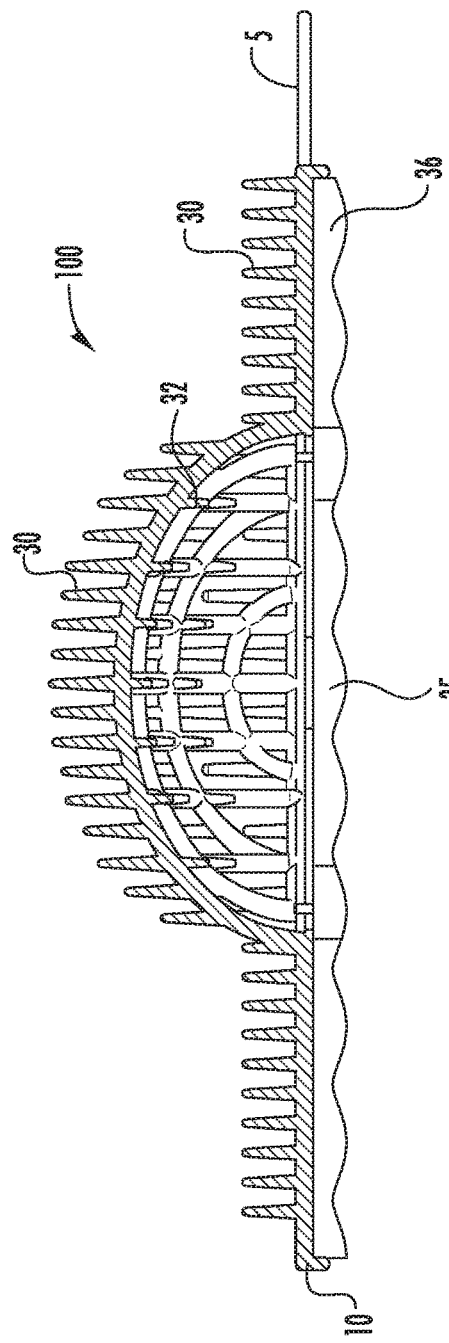

URINAL SCREENS AND ASSEMBLIES

CROSS-REFERENCE TO RELATED APPLICATIONS

This application claims priority benefit of U.S. Provisional Application No. 62/516,078, filed Jun. 6, 2017, which is incorporated by reference herein in its entirety.

BACKGROUND

When a fluid stream is incident upon a urinal, the interaction of the fluid stream and the urinal may cause some of the fluid to splash back toward the user of the urinal. This may cause the user's pants to be splashed and/or cause fluid droplets to end up on the restroom floor. Therefore, urinal screens are often used to reduce the splashing of the fluid, such as back toward the user of the urinal. However, many currently available urinal screens do not sufficiently reduce the splash of the fluid incident upon the urinal. Moreover, many currently available urinal screens trap fluid in the urinal, which may lead to an unpleasant odor. Thus, there is a need for improved urinal screens that provide sufficient splash reduction without trapping fluid within the urinal at a minimal cost.

SUMMARY OF THE DISCLOSURE

In one aspect, a urinal screen is provided, including an outer ring, a web portion bounded by the outer ring and having a first face and an opposed second face, the web portion including a plurality of web strings disposed in a mesh pattern, such that a plurality of open areas are defined among the web strings, and a plurality of posts projecting from the first face of the web portion, wherein the web portion includes a planar portion and a vaulted portion, with the planar portion extending from the outer ring and surrounding the vaulted portion.

In another aspect, a urinal screen is provided, including an outer ring and a web portion bounded by the outer ring and having a first face and an opposed second face, the web portion including a plurality of web strings disposed in a mesh pattern, such that a plurality of open areas are defined between the web strings, wherein the web portion comprises a vaulted portion defining a concave inner surface, wherein a plurality of spacer nubs project from the concave inner surface of the vaulted portion.

In yet another aspect, a urinal screen assembly is provided, including a urinal screen having a vaulted portion and a bioenzymatic block containing odor combatting chemistry disposed in a void formed by the vaulted portion.

BRIEF DESCRIPTION OF THE DRAWINGS

Referring now to the drawings, which are meant to be exemplary and not limiting, and wherein like elements are numbered alike. The detailed description is set forth with reference to the accompanying drawings illustrating examples of the disclosure, in which use of the same reference numerals indicates similar or identical items. Certain embodiments of the present disclosure may include elements, components, and/or configurations other than those illustrated in the drawings, and some of the elements, components, and/or configurations illustrated in the drawings may not be present in certain embodiments.

FIG. 2E is a side view illustrating the urinal screen of FIG. 2A.

FIG. 2F is a cross-sectional view illustrating the urinal screen of FIG. 2A (taken along line 2F as shown in FIG. 2C).

DETAILED DESCRIPTION

The present disclosure provides urinal screens for screening foreign particles from entering the urinal drain, optionally providing a fragrance or other air freshening substance at the point of use, and reducing the splash from a fluid stream generally directed toward the urinal drain. Various aspects of the present disclosure provide urinal screens and associated methods. In one aspect of the present disclosure, a urinal screen for reduced splash back is provided.

Figure 1:
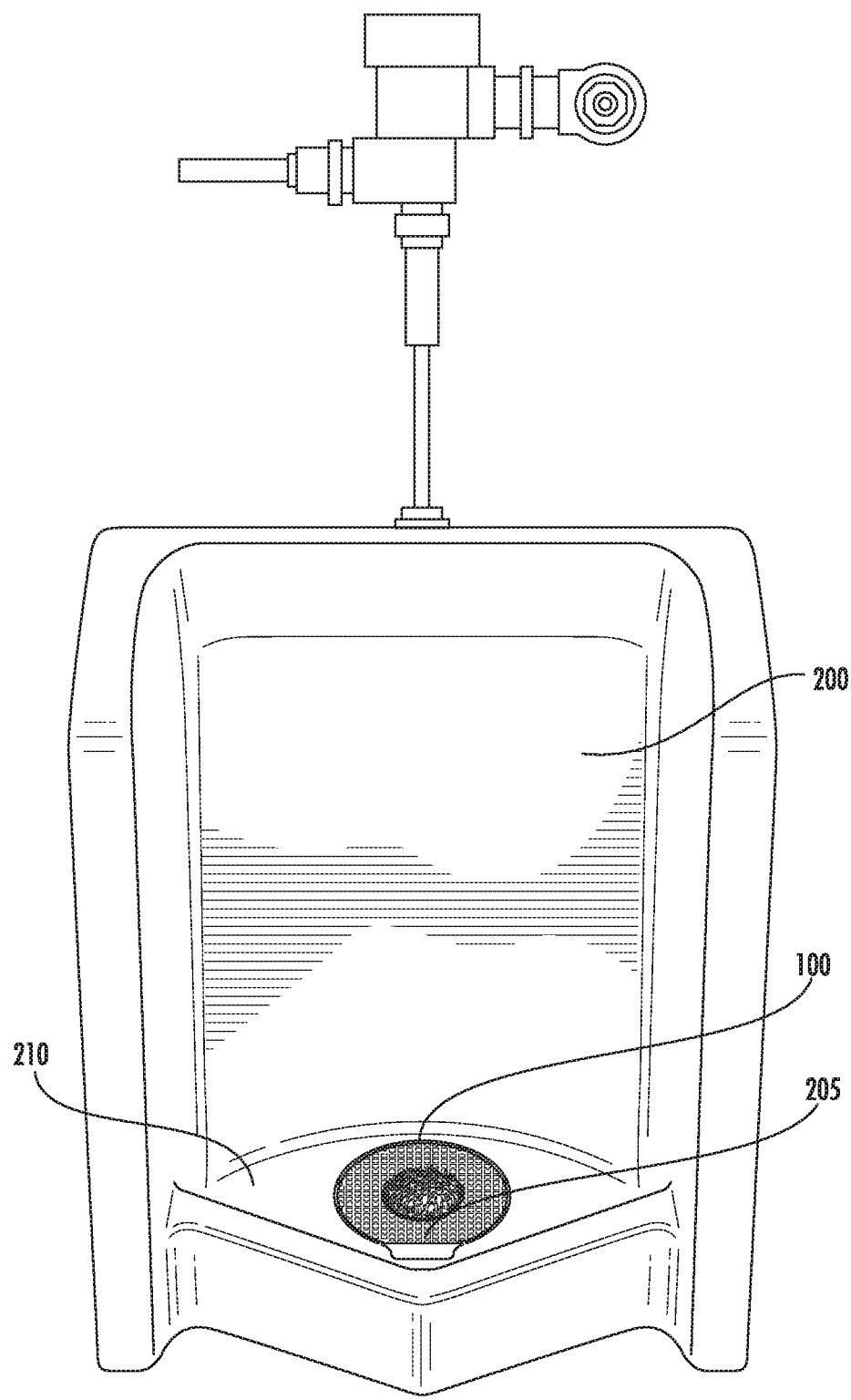
FIG. 1 is a perspective view illustrating a urinal screen according to the present disclosure disposed in a urinal.

FIG. 1 illustrates a urinal screen 100 positioned within a urinal 200 in accordance with the present disclosure. In the depicted embodiment, the urinal screen 100 is positioned on the urinal floor 210 and covers the urinal drain 205. For example, a restroom attendant or maintenance crew member may place a urinal screen 100 in a urinal 200 such that the urinal screen 100 generally covers the urinal drain 205. In various embodiments, the urinal screen 100 may be positioned such that a fluid stream generally directed toward the urinal floor 210 and/or the urinal drain 205 may be at least partially incident upon the urinal screen 100. In various embodiments, the urinal screen 100 may be flexible such that the urinal screen may flex and conform to the geometry of the urinal floor 210. Moreover, the urinal screen 100 may have a minimalist design, providing a high performance, lightweight, and cost efficient urinal screen.

The urinal screen may, in some embodiments, be further configured to funnel the fluid of the fluid stream into the urinal drain 205 without trapping fluid. Moreover, in various embodiments, the urinal screen 100 may be configured to prevent foreign materials (e.g., gum, cigarette butts, or other trash) from entering the urinal drain 205, possibly causing the urinal drain 205 to become clogged. As such, the urinal screen 100 may include a web portion configured to allow fluid to flow through the urinal screen 100 while preventing foreign materials that are large with respect to the web portion from entering the urinal drain 205.

In various embodiments, the urinal screen 100 may be further configured to mask, neutralize, or prevent unpleasant odor. For example, the urinal screen 100 may be configured to prevent fluid from being trapped within the urinal 200. In various embodiments, the urinal screen 100 may be impregnated with a fragrance or other air freshening substance to be released over time.

In various embodiments, the urinal screen 100 is further configured to receive an insert 40 containing odor-combatting chemistry therein. FIGS. 3A-3F illustrate the urinal screen 100 of FIGS. 2A-2F having an insert 40 operably associated therewith. For example, the insert 40 may be a suitable bioenzymatic block, such as are known in the art.

For example, bioenzymatic blocks may be designed to release enzymes and/or bacteria, such as bacillus, into the urinal and associated pipes. In use, the bacillus will change from spores to vegetative and then produce enzymes of their own. Enzymes act as catalysts for reactions including the decomposition of urine. *Bacillus* can also use urea, a component of urine, as a food source. The bacillus will also compete for space in the drains and push out other organisms many of which typically have malodorous byproducts. Additionally, the bacillus may digest biofilms and other organics in the drain that are decomposing and giving off malodors. Further, the bioenzymatic block may help to keep the urinal drain clean. Urine may build up in the drain and cause an odor, but may also create a drainage block due to the uric acid building up in the drain and hardening over time. A suitable descaling agent in the bioenzymatic block may decrease the amount of uric acid collecting in the drain and eliminate other forms of scale (e.g., mineral) that may collect in the drain. Thus, the bioenzymatic composition may contain odor combatting chemistry that destroys a component of urine that lingers in the drain, creating clogs and causing odor. In certain embodiments, the bioenzymatic block contains one or more surfactants and one or more strains of bacillus and their associated enzymes. In some embodiments, the bioenzymatic composition also contains one or more ingredients to prevent the buildup of scale.

In certain embodiments, the bioenzymatic blocks contain any suitable bioenzymatic composition to achieve one or more of the above-described functions. For example, the bioenzymatic blocks may be formed of a suitable carrier material in combination with one or more functional chemistry agents. For example, the block may contain a non-paraben base material containing one or more cleaning chemicals and/or enzymes to attack odor sources. For example, the bioenzymatic blocks may contain any combination of polyethylene glycols of various molecular weights, stearyl ether, cetyl alcohol, phosphonic acid, phosphorous acid, and hydroxyethanediphosphonic acid. For example, any combination of bacteria strains from the following genus/species may be used: *Bacillus subtilis, Bacillus megaterium, Bacillus licheniformis*, and *Bacillus amyloliquifaciens*. For example, these strains may produce and excrete the following enzymes: amylase, protease, lipase, and bacterial cellulase.

Figure 3A:
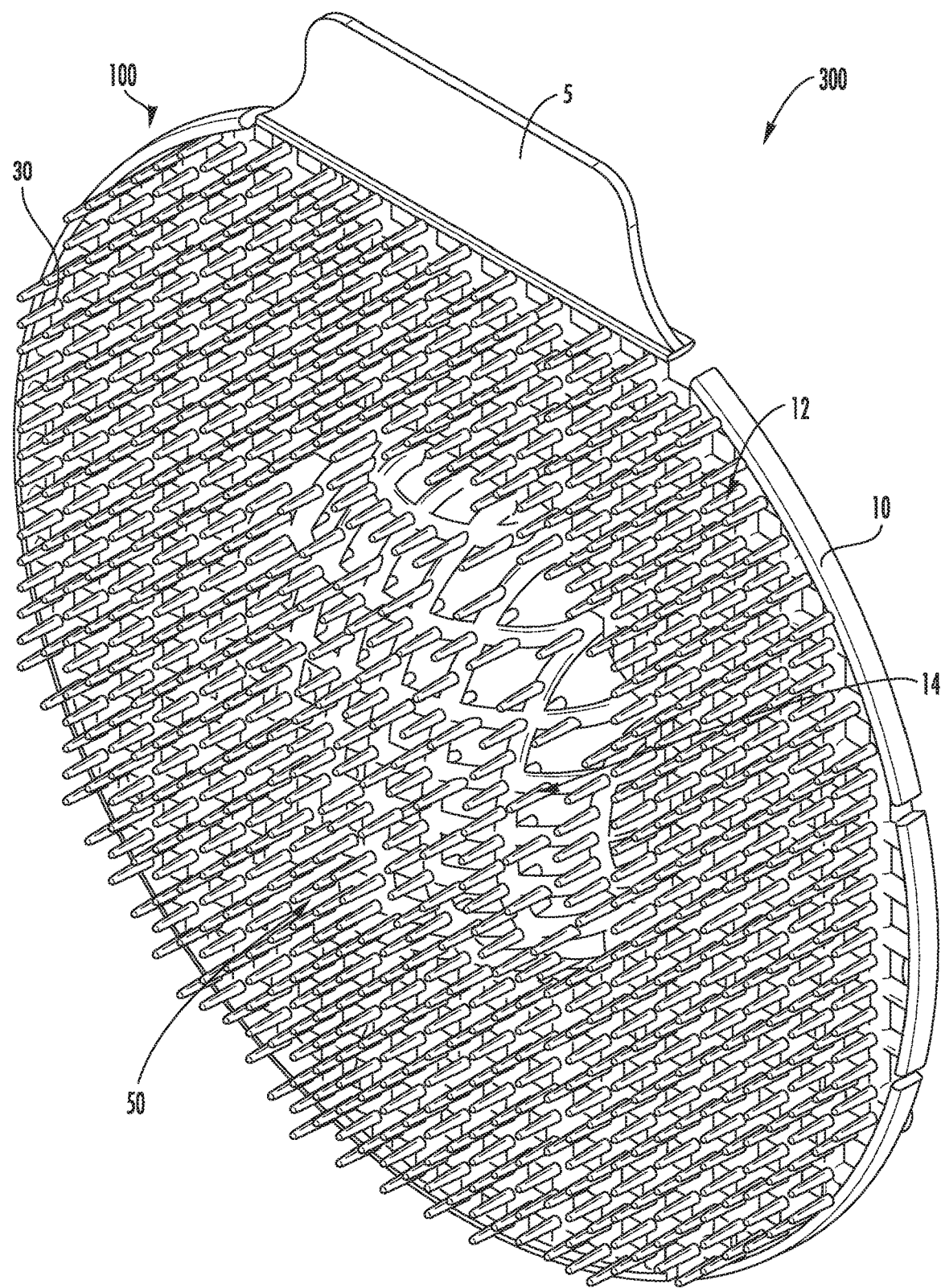
FIG. 3A is a perspective upper view illustrating a urinal screen with a bioenzymatic block, according to the present disclosure.
Figure 3B:
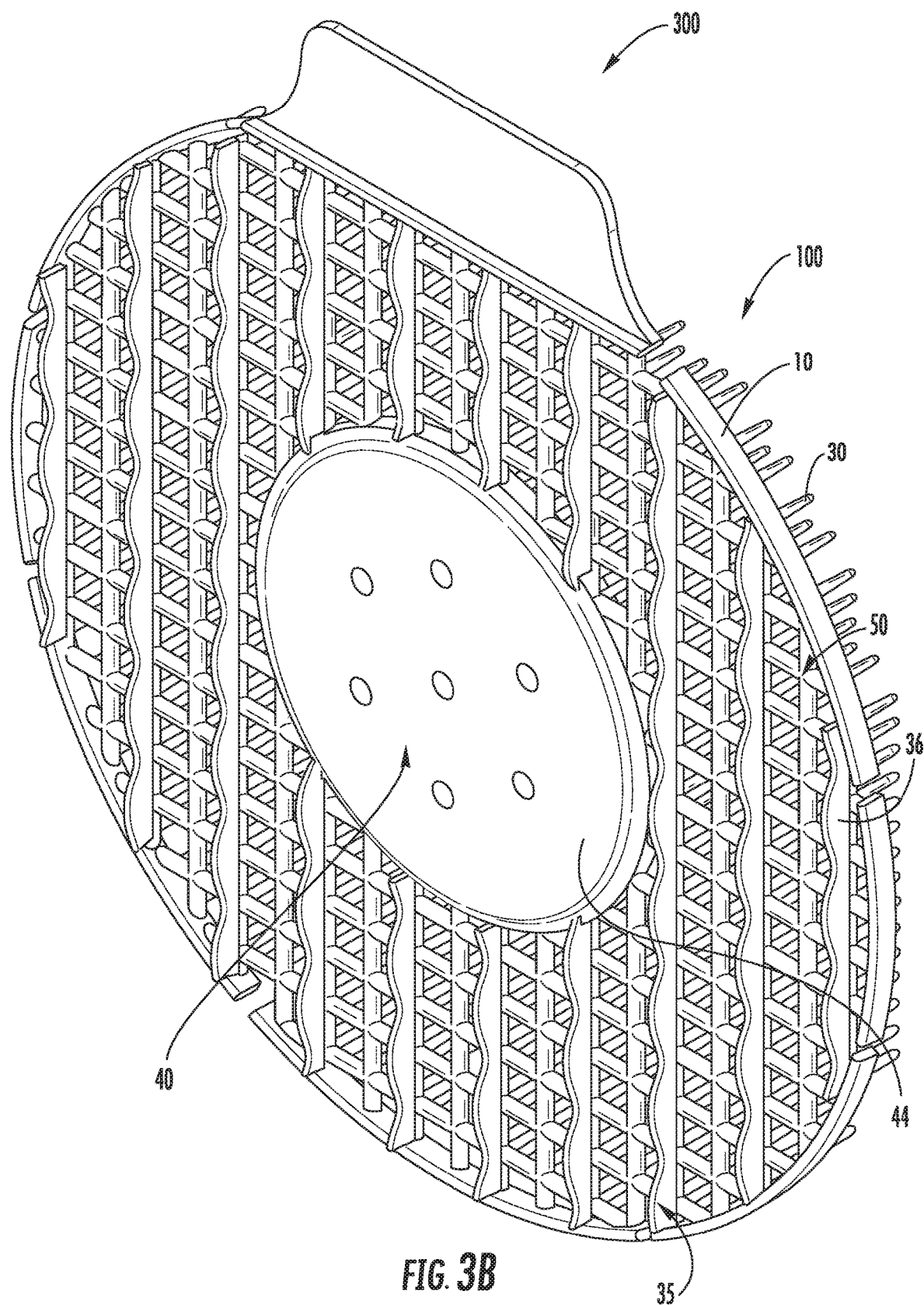
FIG. 3B is a perspective lower view illustrating the urinal screen of FIG. 3A.
Figure 3C:
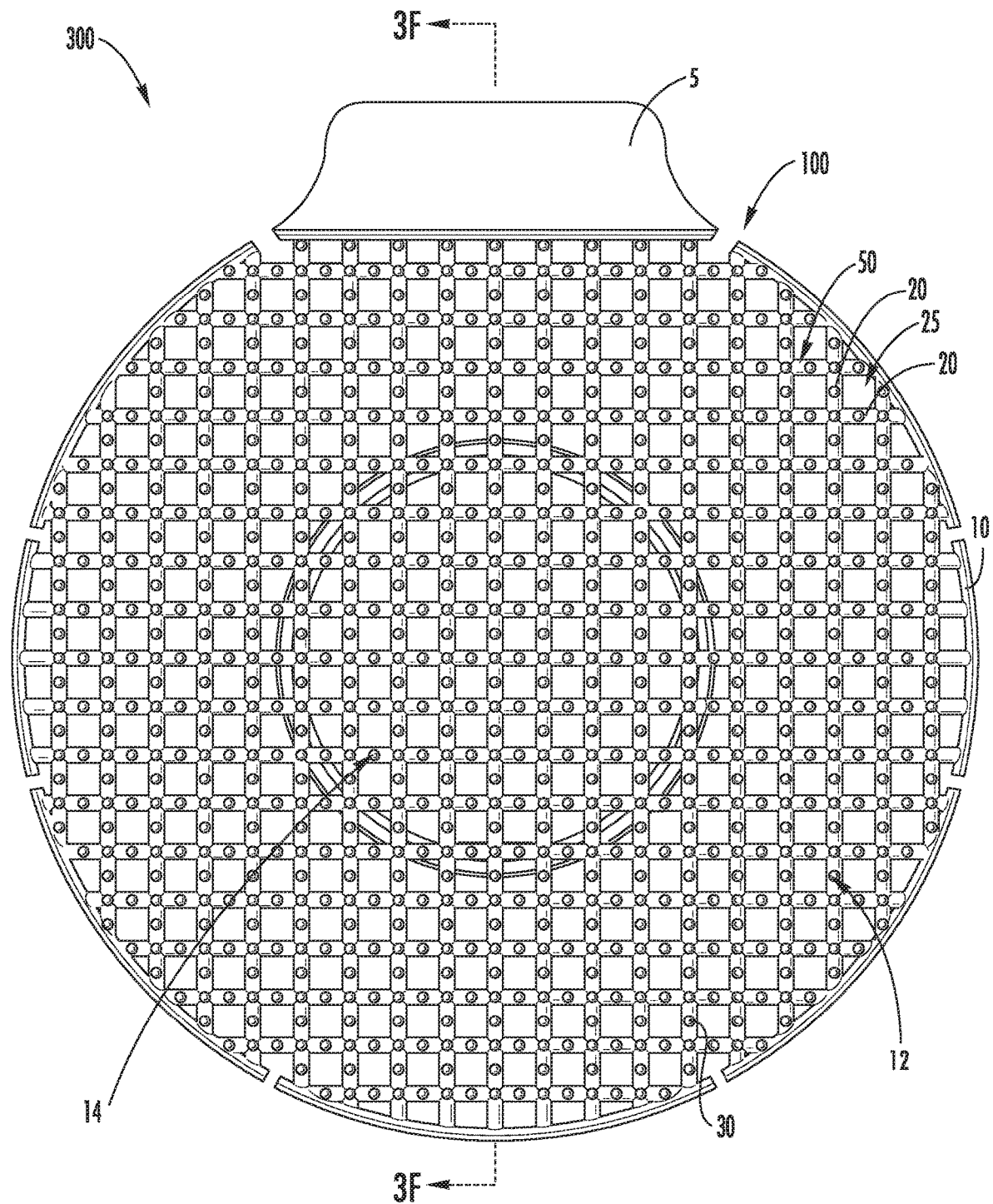
FIG. 3C is an upper plan view illustrating the urinal screen of FIG. 3A.
Figure 3D:
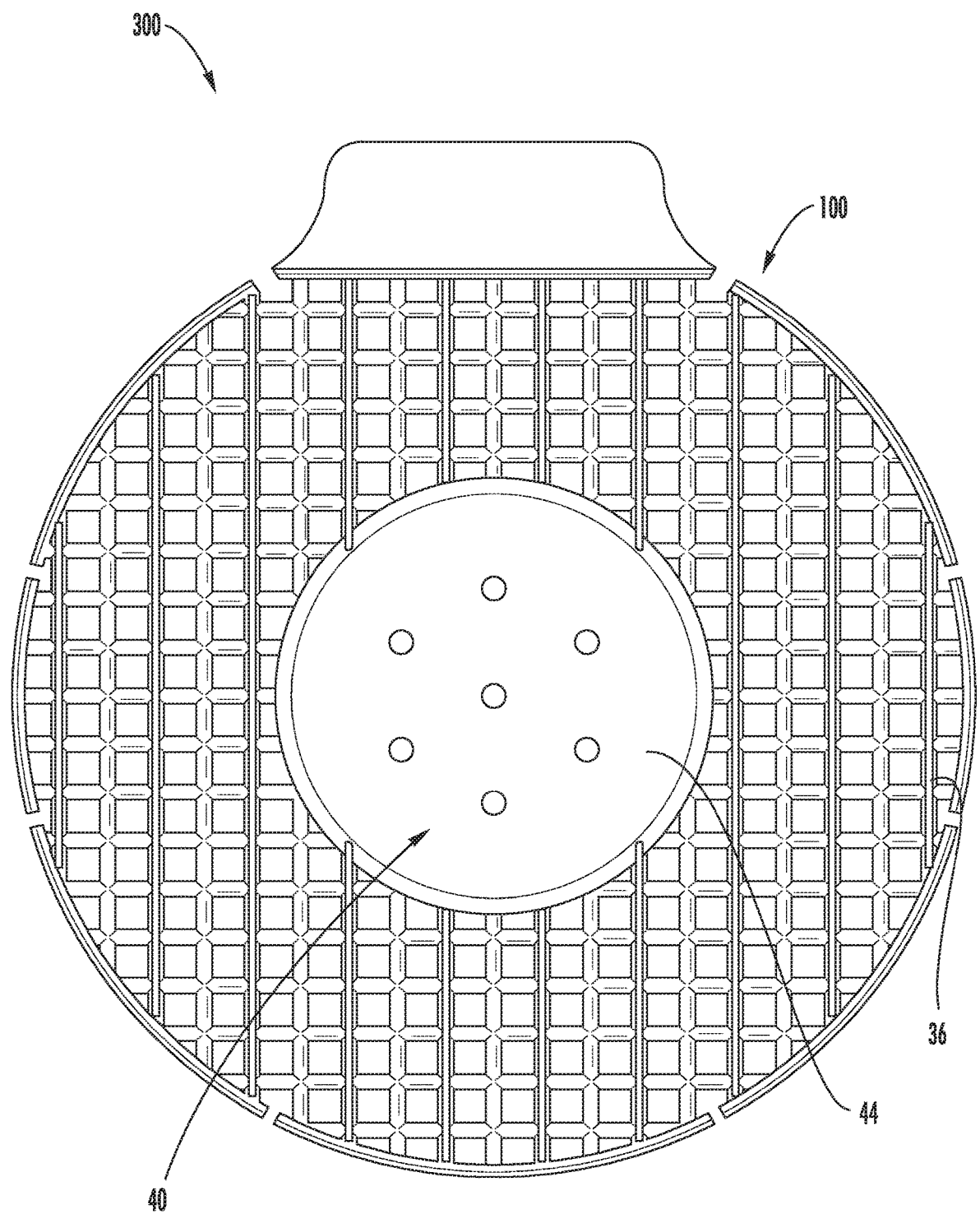
FIG. 3D is a lower plan view illustrating the urinal screen of FIG. 3A.
Figure 3E:
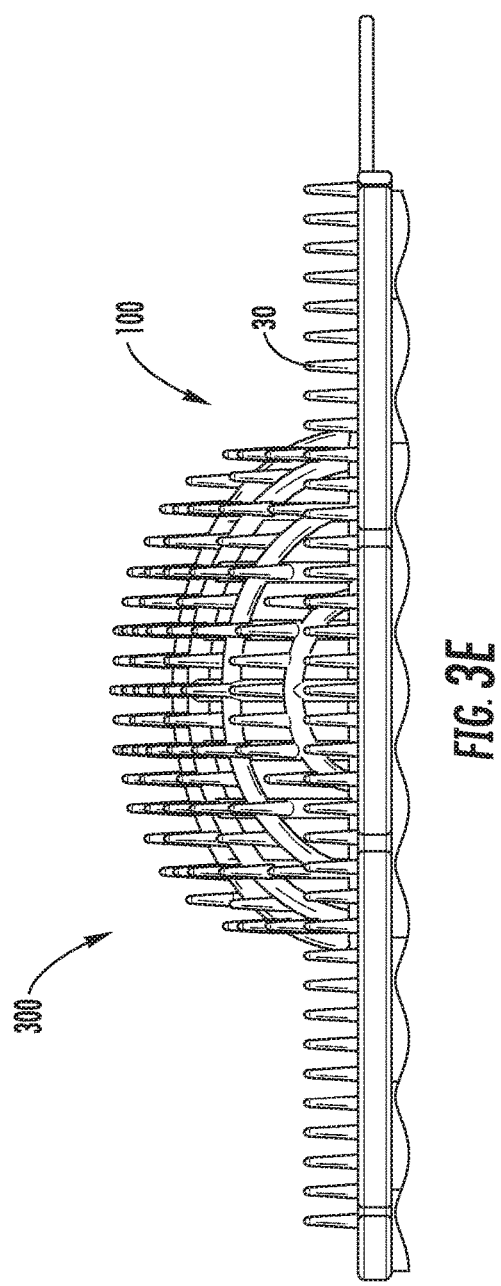
FIG. 3E is a side view illustrating the urinal screen of FIG. 3A.
Figure 3F:
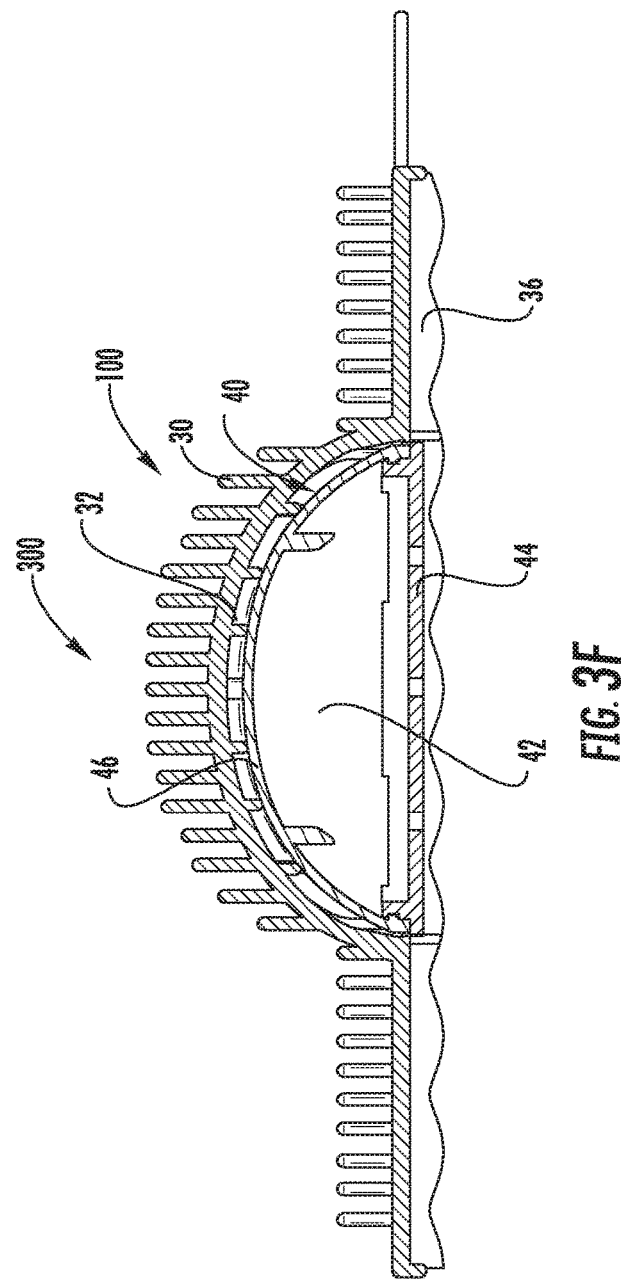
FIG. 3F is a cross-sectional view illustrating the urinal screen of FIG. 3A (taken along line 3F as shown in FIG. 3C).

In certain embodiments, as shown in FIGS. 3B, 3D, and 3F, the insert 40 may include a rigid shell or cover (e.g., base 44 and top 46) that surrounds a block 42 containing the odor combatting or other suitable chemistry. In other embodiments, the insert 40 includes the block 42 without a cover. In embodiments in which the insert 40 includes a cover, the base 44 may include one or more apertures for exposing the block 42 to the environment (e.g., atmosphere) surrounding the insert 40. For example, such apertures may allow a volatile, dissolvable, and/or degradable agent contained within the block to be released through the apertures.

Traditionally, the active agent-containing blocks 42 of these inserts 40 are susceptible to common cleaning products such as bleach. Additionally, the insert 40 may be configured to provide controlled release of the bioenzymatic composition of the block 42. For example, the cover and the apertures of the base may limit the release of the composition by preventing urine or other liquid from dissolving the block from the upper side and limiting release from the bottom side. For example, urine may enter through the openings on the base of the insert and interact with the block to dissolve a portion of the block and release some of the bioenzymes or other functional agents into the drain. Thus the size, shape, and spacing of the openings can be selected to control the rate of dissolution of the block to achieve the desired effectiveness of drain cleaning and expected life for the screen.

Thus, the above-described shell or cover may be used to protect the block from such cleaning agents that may be poured over the urinal screen during maintenance. The cover or shell may be formed from any suitable waterproof materials, such as polypropylene, HDPE, or other plastics. Regardless of whether the insert contains a cover, the generally flat surface(s) of traditional inserts typically cause splashing of liquid impinging on the urinal screen.

For example, it has been discovered that providing an insert 40 having at least a partially rounded outer profile significantly reduces splashing from liquid that contacts the insert surface. Further, such inserts 40 having at least a portion of their surface with a rounded profile may be combined with the urinal screens 100 described herein, which have a web portion 50 including at least some rounded surfaces on its first (e.g., upper) face. In certain embodiments, the web portion 50 forms a vaulted portion 14 that is configured to receive and cover the insert 40. Thus, the web portion 50 covering the insert 40 may also provide further splash reduction at the surface over the insert. Such urinal screen assemblies may beneficially provide reduced splashing in combination with the odor combatting or other effects of the insert and its chemistry containing block.

Figure 2A:
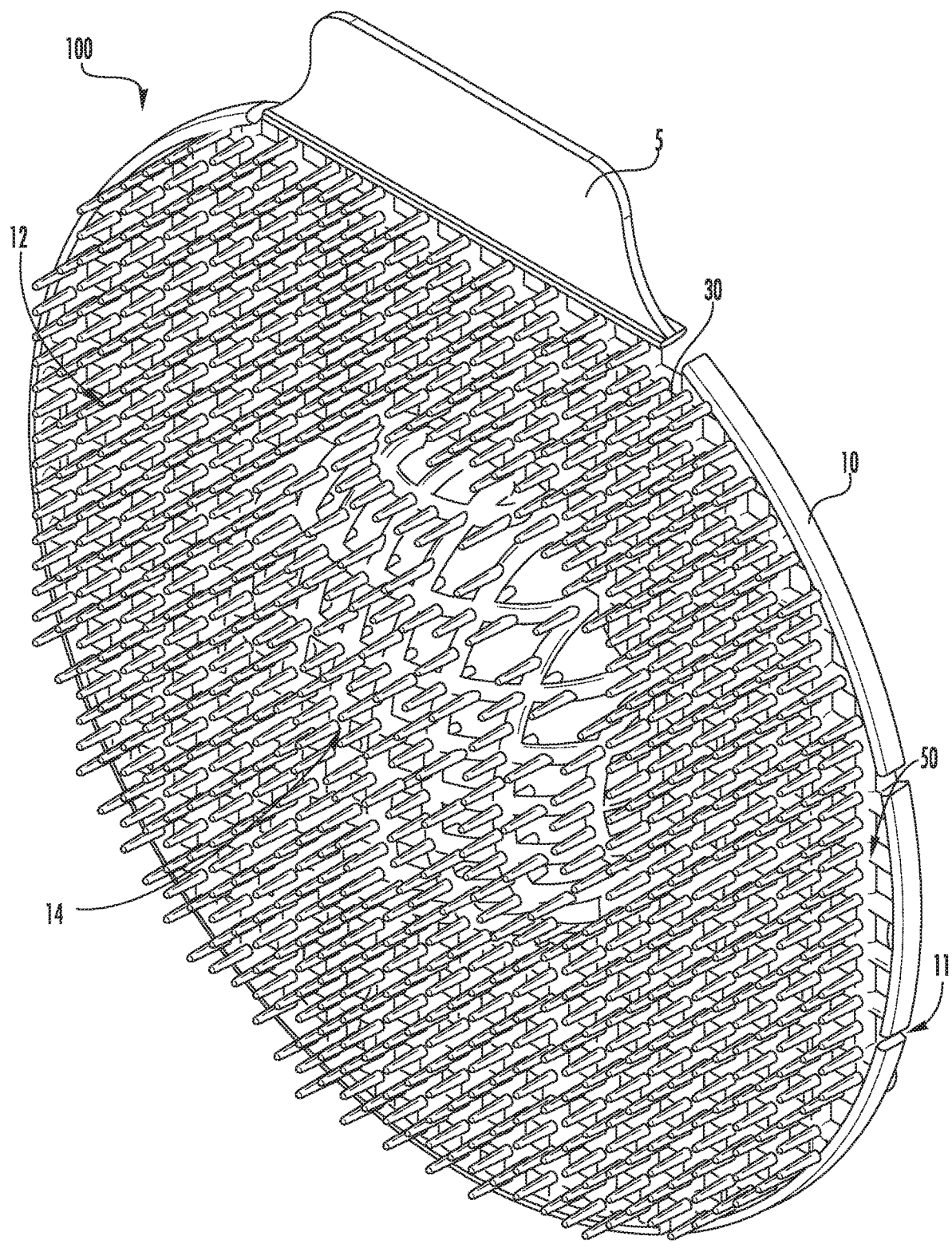
FIG. 2A is a perspective upper view illustrating a urinal screen according to the present disclosure.
Figure 2B:
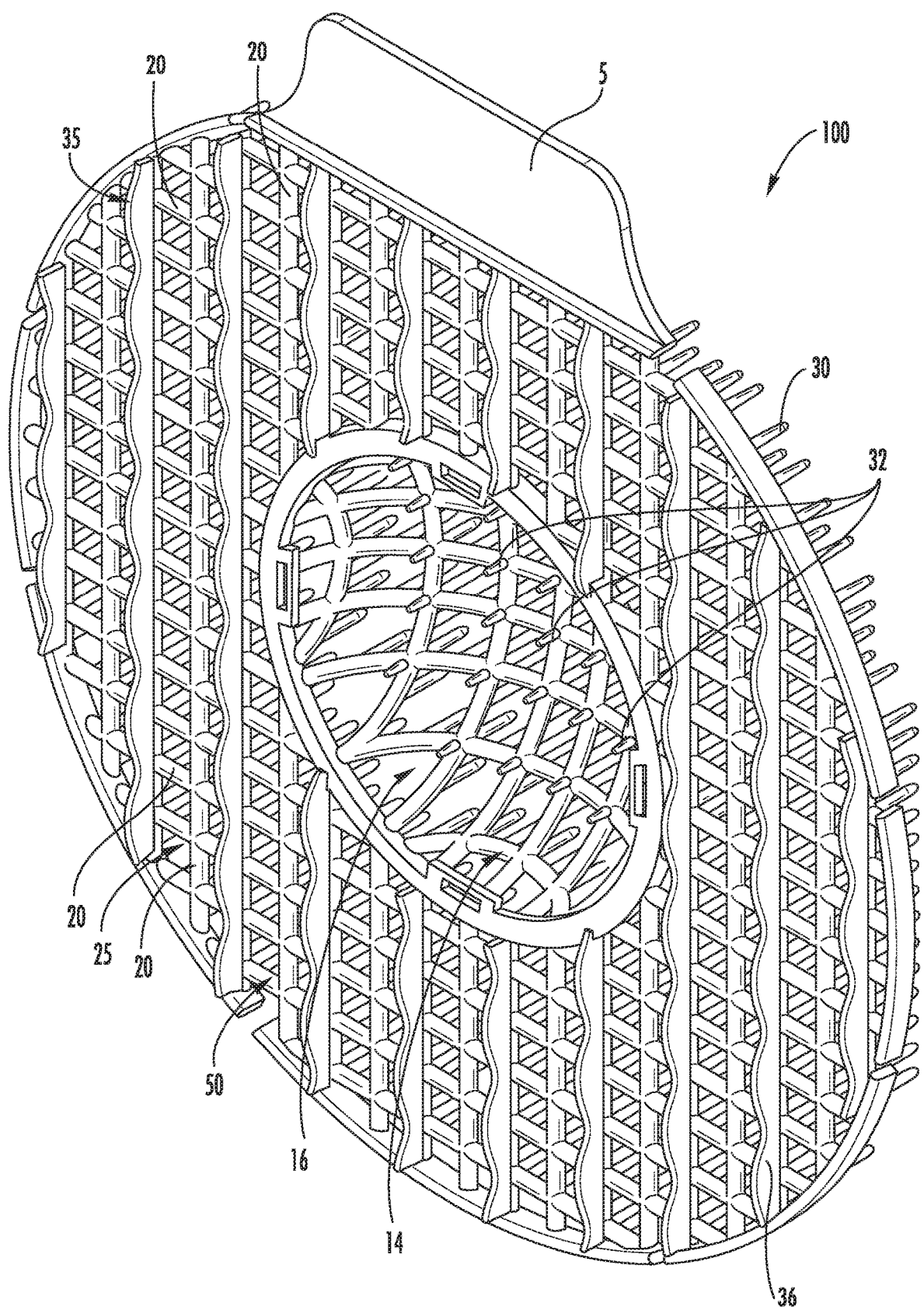
FIG. 2B is a perspective lower view illustrating the urinal screen of FIG. 2A.

In certain embodiments, as shown in FIG. 2B, the urinal screens 100 further contain spacer nubs (e.g., posts, rods, projections) 32 disposed on the inner surface 16 of the vaulted portion 14. That is, a plurality of spacer nubs 32 may be disposed on the concave inner surface of the vaulted portion. As used herein the phrase "concave inner surface" refers to the surface of the vaulted portion forming the second face of the web portion of the urinal screen (i.e., the surface of the vaulted portion that is configured to face the surface of the urinal (floor and/or drain) when the urinal screen is deployed in a urinal). It should be understood that any of the shapes and configurations of the vaulted portion described herein may have a concave inner surface, and that the phrase is not meant to be limited to hemispherical or otherwise dome-shaped vaulted portions.

Figure 5:
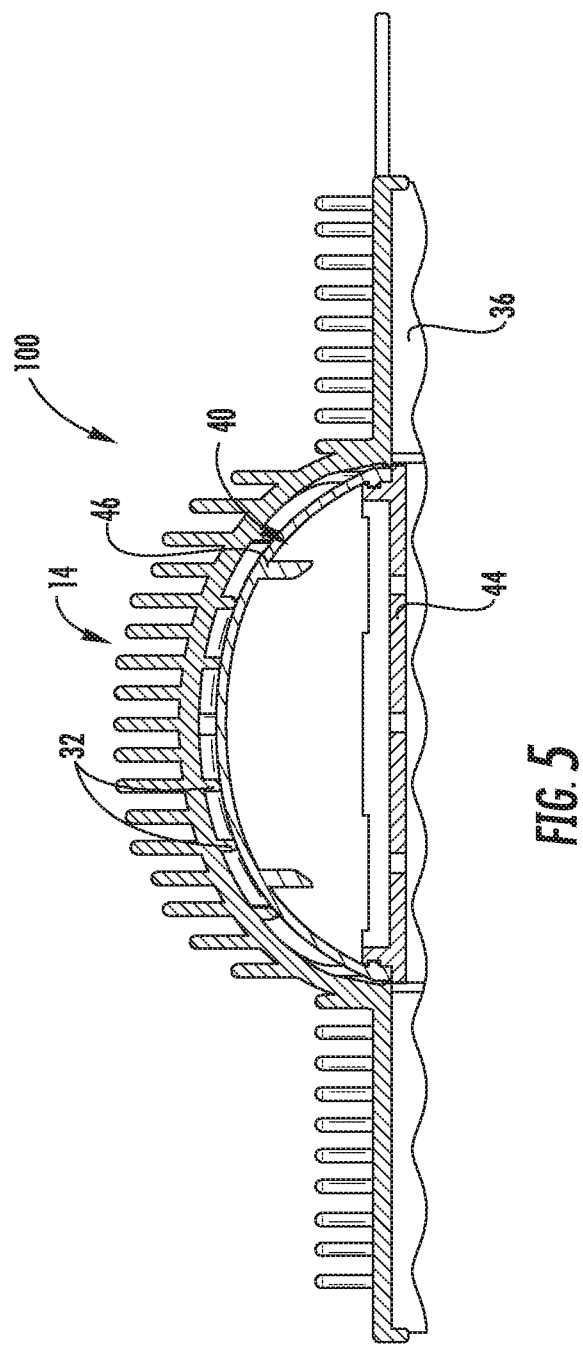
FIG. 5 is a cross-sectional view illustrating a urinal screen with a bioenzymatic block, according to the present disclosure.

The spacer nubs 32 may be sized, shaped, and otherwise configured to provide a standoff or gap between the upper surface of the insert 40 (e.g., top of insert shell/cover 46 or upper surface of an uncovered insert block) and the web strings 20 of the web portion 50, as will be described below. As illustrated in FIG. 5, such standoffs were discovered to significantly reduce pooling of liquid between the top surface 46 of the insert 40 and the web strings 20 forming the vaulted portion 14 of the web, relative to embodiments not having such spacer nubs.

In various embodiments, the urinal screen 100 may be configured to reduce splashing of the fluid stream incident thereon. For example, the urinal screen 100 may be configured to reduce the amount of fluid that is splashed back away from the urinal floor, out of the urinal, and/or the like from an incident fluid stream. In various embodiments, the urinal screen 100 may be configured to diffuse, deflect, and/or the like the fluid stream incident thereon. For example, the urinal screen 100 may have a reduced area of (e.g., may not have any) surfaces that are substantially flat to the user's view (i.e., in plan view) such that any fluid droplets that may splash off of the urinal screen 100 are not directed back toward the user. For example, the urinal screen 100 may be configured to deflect portions of the fluid stream incident thereon into urinal 200.

For example, it has been discovered that splash back may be reduced by providing a urine receiving face of the urinal screen 100 that has a reduced amount of flat surfaces for an impinging stream of urine to contact. That is, the urinal screens 100 of the present disclosure may include surfaces having a rounded profile on a face of the urinal screen 100 configured to receive urine during use. In some embodiments, alone or in combination with reduction of flat surfaces of the urinal screen 100, splash reduction also may be achieved by the inclusion of a plurality of posts 30 that project upward from the urine receiving face of the urinal screen 100 and serve to absorb some of the momentum of a splashed fluid stream and redirect the fluid back toward the urinal floor. Various embodiments of urinal screens having these features are described herein; however, it should be understood that embodiments of the disclosure may include only some of the described features or combinations of these features not explicitly described herein. Additional features of the urinal screens described herein are disclosed in U.S. patent application Ser. No. 15/285,951, filed on Oct. 5, 2016 (published as U.S. Patent Application Publication No. 2017/0096808 on Apr. 6, 2017), which is incorporated by reference herein in its entirety.

Figure 4:
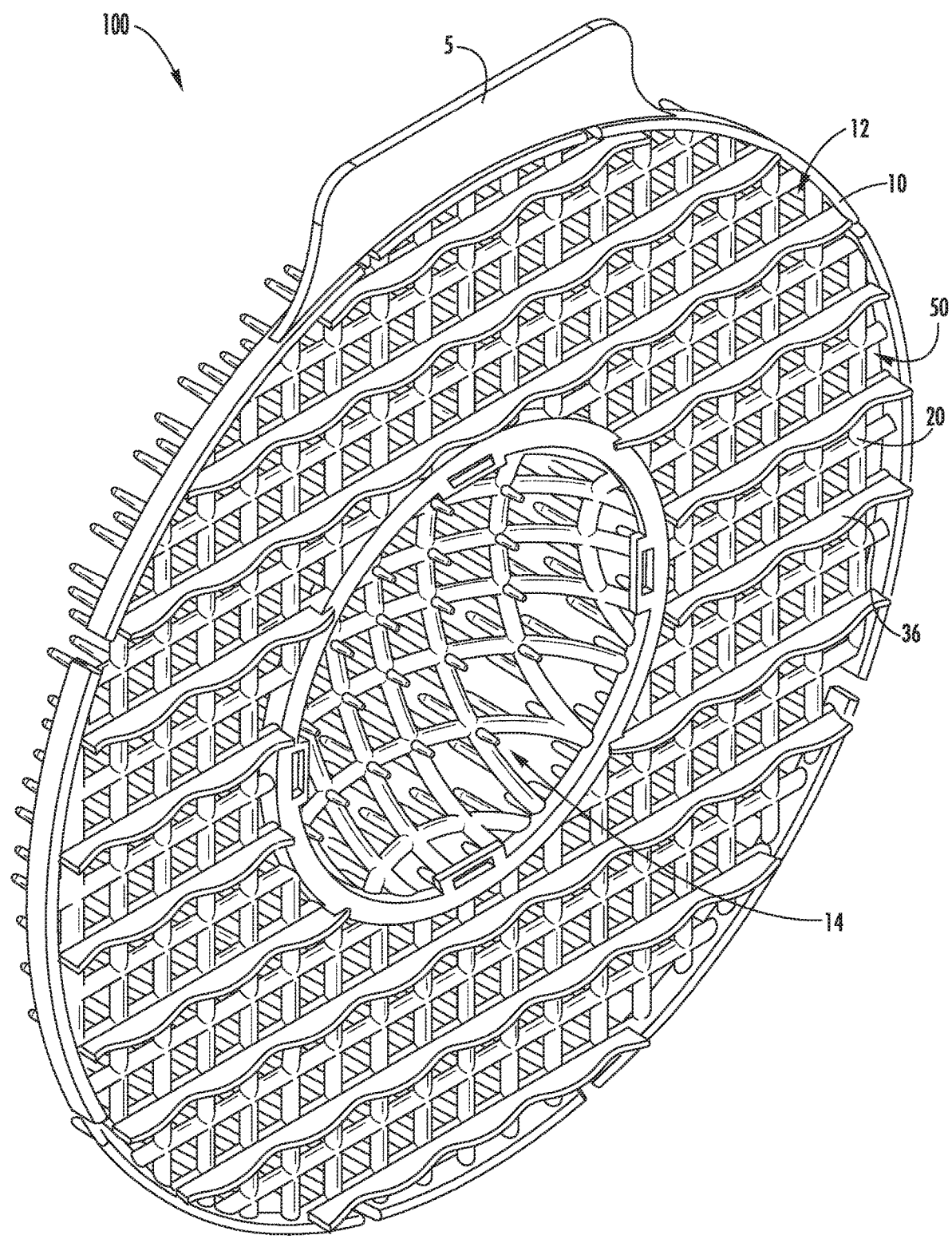
FIG. 4 is a perspective lower view illustrating a urinal screen according to the present disclosure.

In certain embodiments, as shown in FIGS. 2A-2F, a urinal screen 100 includes an outer ring 10 and a web portion 50 bounded by the outer ring 10. The web portion has a first face (e.g., a urine receiving face) and an opposed second face (e.g., a urinal contacting or fronting face) and is formed from a plurality of web strings 20 disposed in a mesh pattern, such that a plurality of open areas 25 are defined between the web strings 20. As used herein, the phrase "outer ring" refers to the peripheral rim of the urinal screen that provides structural support for the web portion it bounds. The ring may be any suitable size and shape, such as substantially circular, elliptical, square, rectangular, polygonal (e.g., octagonal, hexagonal, pentagonal), irregular, or novelty shaped. The outer ring 10 may be integral with or distinct from the web strings 20 of the web portion 50. In some embodiments, the outer ring 10 may include a tab 5 that may be configured to act as a handle, labelling area, or the like. Various embodiments of the tab 5 are shown in FIGS. 2A and 4.

As used herein, the phrase "web strings" refers to elongated cross-members or strands that form the mesh screen of the web portion of the urinal screen. The web strings may have any suitable size and cross-sectional shape, including circular or elliptical.

In certain embodiments, as shown in FIGS. 2A and 2B, the web portion 50 includes a substantially planar portion 12 and a vaulted portion 14, with the substantially planar portion extending from the outer ring 10 and surrounding the vaulted portion 14.

As used herein, the phrase "substantially planar," when used to describe the web portion, or a portion thereof, refers to the web portion having a generally flat shape or lying in a two-dimensional plane. That is, the substantially planar portion of the web portion is generally not domed, vaulted, or otherwise three-dimensionally shaped. However, as will be described in greater detail, the web portion may have a woven or faux-woven design, such that the web portion is generally two-dimensional, but has a slight three-dimensional character. Such woven and faux-woven web portions should be understood to be substantially planar within the scope of this disclosure.

In certain embodiments, as shown in FIG. 2A, the substantially planar portion 12 and the vaulted portion 14 are integrally formed, such as by a molding process. In other embodiments, the substantially planar portion 12 and the vaulted portion 14 may be separate elements that are bonded or otherwise coupled to one another.

As shown in FIG. 2B, in certain embodiments the vaulted portion 14 is a dome or hemisphere. That is, the portion of the web portion 50 forming the vaulted portion 14 is formed in the shape of a dome or hemisphere. In some embodiments, the dome is a spherical cap in which the height of the cap is less than the radius of the imaginary sphere cut by the imaginary plane of the planar portion of the web portion. In other embodiments, the vaulted portion 14 is a frustocone or a cylinder. For example, the vaulted portion 14 may be formed from any combination of angled or straight sidewalls, relative to a plane extending perpendicularly to the substantially planar portion 12, and a domed or flat top wall.

As used herein, the phrase "mesh pattern" refers to the web strings 20 of the web portion 50 being arranged in an interwoven or intertwined configuration forming open spaces between the strings, such as a net configuration. The terms "mesh" and "woven" refer to the appearance and properties of the web strings, but does not mean that the web strings are in all embodiments separate, overlapping structures. On the contrary, the web strings may be integrally formed (e.g., as a monolithic structure), such as by a molding process.

In some embodiments, at least the portions of the web strings 20 forming the urine receiving face of the web portion 50 are substantially rounded in profile. As used herein, the term "rounded in profile" refers to the relevant surface having a curved, non-flat contour. For example, such rounded surfaces may be configured to receive a downward stream of urine such that the impinging stream does not contact a flat surface and the resulting splash is minimized.

FIGS. 2A-2F and 4 provide various views of a urinal screen 100 in accordance with various embodiments of the present disclosure. In the illustrated embodiments, the urinal screen 100 is generally circular. However, other shapes may be used. For example, the urinal screen 100 may be generally elliptical, square, rectangular, polygonal, irregular, or novelty shaped. For example, the urinal screen 100 may be shaped like a fish or other animal in order to hold the attention of younger users. In general, urinal screen 100 may be sized appropriately to cover the urinal drain 205 and at least a portion of the urinal floor 210. For example, the urinal screen 100 may be approximately four to eight inches across (e.g., in diameter). For example, in one embodiment, the urinal screen 100 is from about 3 inches to about 8 inches in diameter. For example, the urinal screen 100 may be from about 6 inches to about 7 inches in diameter. For example, the urinal screen 100 may be from about three inches to about five inches in diameter. As used herein, the term "about" when used to modify a particular amount is used to refer to plus or minus 2 percent of the amount being modified.

In various embodiments, the urinal screen 100 includes an outer ring 10. The outer ring 10 is configured to provide structural support for the urinal screen 100. In various embodiments, the outer ring 10 may be elliptical or round in cross-section. In various embodiments, as shown in FIG. 2A, the outer ring 10 may include outer ring gaps 11. The outer ring gaps 11 may be small breaks in the outer ring (e.g., 1 mm to 1 cm in length). In various embodiments, the outer ring gaps 11 may be configured to allow the outer ring 10 to provide structural support for the urinal screen 100 while allowing the outer ring 10 to be flexible enough to conform to a generally arbitrary geometry or contour of a urinal floor 210. In some embodiments, the outer ring 10 may include a tab 5 that may be configured to act as a handle or the like. For example, the tab 5 may act as a billboard and provide information identifying the manufacturer and/or providing manufacturer contact information.

In various embodiments, the urinal screen 100 includes a web portion 50. The web portion 50 includes a plurality of web strings 20. The web strings 20 may be woven or have a grid-like, woven, or semi-woven appearance. For example, the web strings 20 may appear to be woven over and under each other as the warp and weft of a plain weaving. That is, the mesh pattern of the web portion 50 may be a plain weave pattern or other suitable weave pattern. In certain embodiments, the web strings 20 have a wavy shape and intersect orthogonally in a way that makes the web strings 20 appear to be woven together.

In this manner, the web strings 20 are not flat from the perspective of the urinal user (i.e., in plan view). For example, the outer ring 10 defines an imaginary flat, two-dimensional plane. Each web string 20 is at an angle with respect to the imaginary plane. Thus, the web portion 50 is inherently three-dimensional, though, as described above, at least a portion thereof (i.e., the planar portion) should be understood as being substantially planar. Moreover, the angle between the imaginary plane and each web string 20 changes constantly along the length of the web string 20. For example, at two nearby points along a web string or adjacent web strings, the gradient fields at the two points will be different. In various embodiments, the web strings 20 may be round (e.g., circular or elliptical) in cross-section. Thus, in certain embodiments, the web portion 50 may be configured such that there are no shoulders, flat surfaces, or inside corners off of which a fluid stream may splash. Moreover, such a design encourages flow of the urine toward the urinal drain without significant splash back.

Figure 2C:
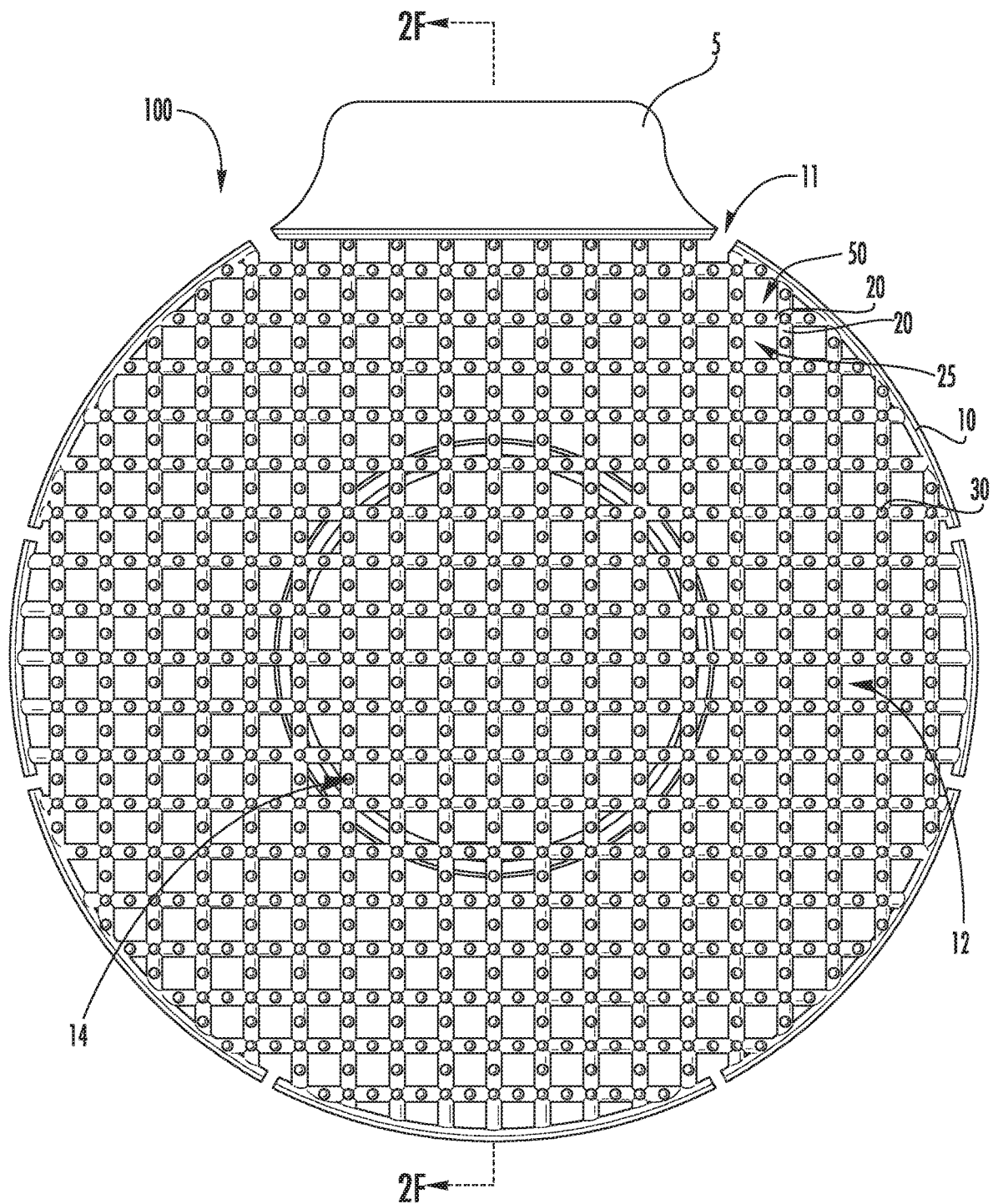
FIG. 2C is an upper plan view illustrating the urinal screen of FIG. 2A.

In certain embodiments, the mesh pattern of the substantially planar portion 12 is continuous to form both the substantially planar portion 12 and the vaulted portion 14. That is, at a transitional region at which the planar portion 12 and the vaulted portion 14 intersect, the web strings 20 may be continuously formed, such as through a molding process. As shown in FIGS. 2B and 2C, in certain embodiments, the web strings 20 may form the vaulted portion such that the mesh pattern and the open areas formed thereby are consistent between the substantially planar portion 12 and the vaulted portion 14, when viewed in plan view (as in FIG. 2C).

The web strings 20 may be arranged (e.g., woven) in such a way as to provide open areas (e.g., holes or apertures) 25 in the web portion 50 configured to allow the fluid of the stream to pass through the urinal screen 100. However, the open areas 25 may be configured to be small enough not to allow large foreign items to enter the urinal drain 205.

The open areas 25 may have any suitable size and shape. In certain embodiments, the open areas of the web portion 50 have a major dimension of approximately 5 mm to 2 cm. As used herein, the phrase "major dimension" refers to the largest diameter, axis length, or side length of the open area when viewed in plan view. In some embodiments, the open areas of the web portion have a major dimension of from about 1 mm to about 30 mm in plan view. For example, the open areas of the web portion may have a major dimension of from about 5 mm to about 10 mm in plan view. For example, the open areas of the web portion may have a major dimension of from about 5 mm to about 7 mm in plan view. For example, the open areas of the web portion may have a major dimension of about 6.5 mm in plan view.

Figure 2D:
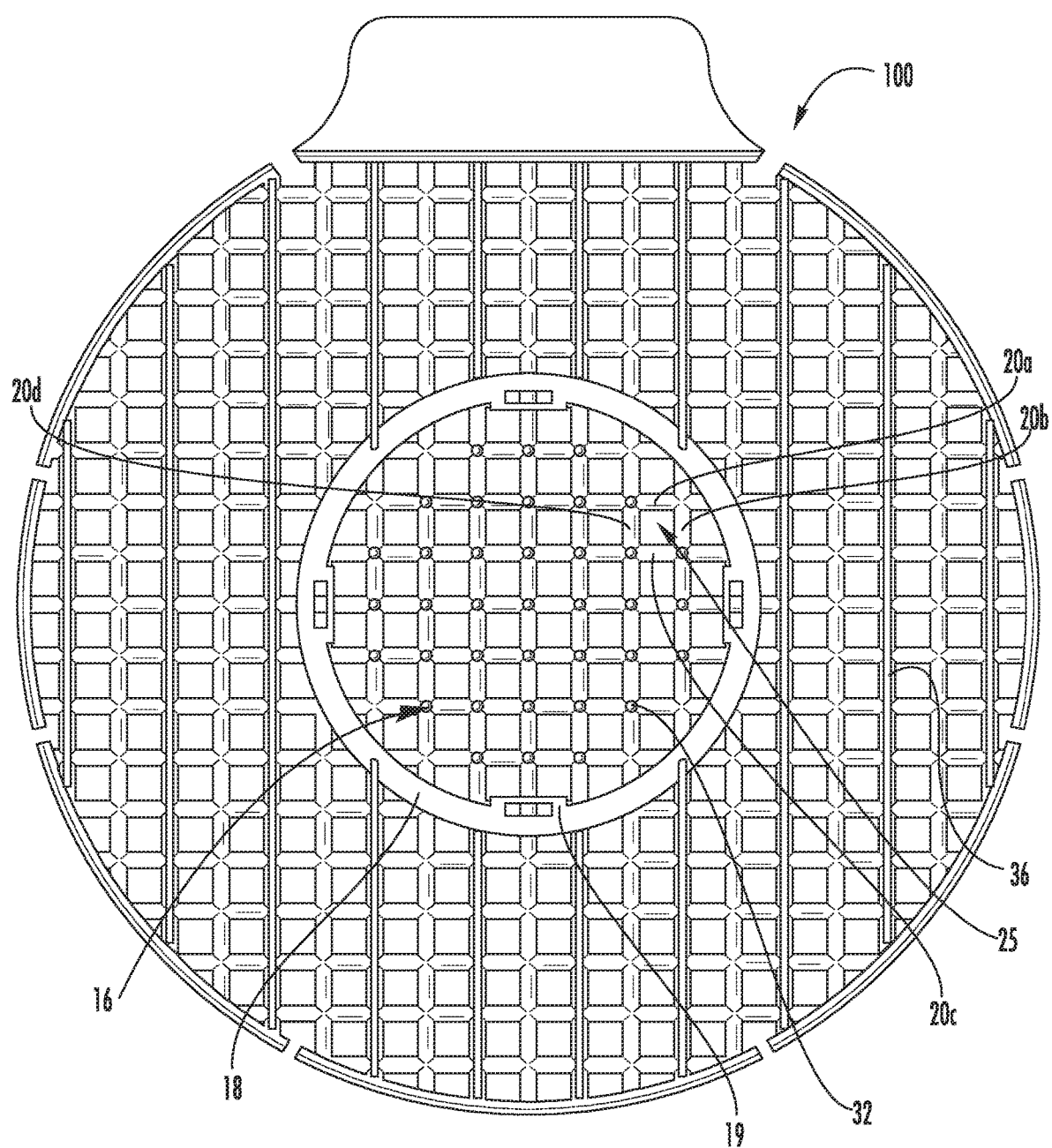
FIG. 2D is a lower plan view illustrating the urinal screen of FIG. 2A.

In certain embodiments, as shown in FIGS. 2C, 2D, 3C, and 3D, the open areas 25 may be generally square or rectangular in shape when viewed in plan view. In some embodiments, the open areas are polygonal in shape, but have rounded (i.e., filleted) corners. In other embodiments, the open areas 25 are circular or elliptical in shape. In certain embodiments, as shown in FIG. 2D, each open area 25 is defined by four web strings (20a, 20b, 20c, 20d). In such embodiments, the open area 25 may be square in shape. In some embodiments, a portion of the open areas have a first size and shape, while a portion of the open areas have a second size and shape. For example, the mesh pattern of the web portion may be formed such that the web strings define a plurality of polygonal (e.g., hexagonal, octagonal) open areas and a plurality of other opens areas (e.g., square) formed between the web strings defining the polygons.

In certain embodiments, when viewed in plan view, the open areas 25 of the urinal screen 100 may occupy from about 25 percent to about 50 percent of the surface area of the urinal screen 100. For example, the open areas 25 of the urinal screen 100 may occupy from about 35 percent to about 45 percent of the surface area of the urinal screen 100. For example, the open areas 25 of the urinal screen 100 may occupy from about 35 percent to about 40 percent of the surface area of the urinal screen 100.

In certain embodiments, as shown in FIG. 2D, the plurality of web strings 20 includes a first set of the web strings 20a, 20c that are substantially parallel to one another and a second set of the web strings 20b, 20d that are substantially parallel to one another and are substantially perpendicular to the first set of web strings 20a, 20c. As mentioned herein, such web strings may be formed in a woven or faux-woven pattern.

In various embodiments, alone or in combination with the rounded profile web strings 20 of the web portion 50, a urinal screen 100 may include a plurality of posts 30 projecting from the first face (e.g., the urine receiving face) of the web portion 50 (e.g., from the substantially planar portion 12 and/or the vaulted portion 14). As shown in FIGS. 2A-C and 2E-F, the first face of the web portion 50 may have a plurality of posts (e.g., nubs, spikes, projections, or grass blades) 30 extending therefrom. For example, a post 30 may be positioned at each node of the web (e.g., where two web strings 20 intersect). In another example, a post 30 may be positioned at the midpoint between each adjacent pair of nodes of the web portion 50. As shown in FIG. 2C, in some embodiments, a post 30 may be positioned at each node of the web and at the midpoints between each adjacent pair of nodes of the web. In other embodiments, a variety of post 30 arrangements may be utilized. For example, in one embodiment, there are approximately twenty posts 30 per square inch on the first face of the urinal screen 100.

The posts may be of any suitable size and shape. In various embodiments, each post 30 may have a height of between 0.5 mm and 1 cm. For example, in one embodiment, each post is approximately 2.5 mm in height. In various embodiments, each post 30 is the same length. In various embodiments, each post 30 is generally round (e.g., circular or elliptical) in cross-section. In some embodiments, as shown in FIG. 2F, each post 30 has a substantially rounded tip and a substantially rounded profile. That is, both the tip and the body of the post 30 may have surfaces with a curved, non-flat contour.

In various embodiments, the urinal screen 100 is configured to deflect a fluid stream incident thereon into a urinal. A portion of the fluid stream passes through open area 25 and splashes off of the urinal floor 210. The splashed fluid stream may be incident upon a post 30, which may absorb some of the momentum of the splashed fluid stream and redirect the fluid back toward the urinal floor 210. Once the fluid has settled onto the urinal floor 210, the fluid may flow freely along the urinal floor 210 into the urinal drain 205. Similarly, if a portion of a fluid stream is incident upon a web string 20 or post 30, the web string 20 or post 30 may deflect the fluid stream through an open area 25 by absorbing at least a portion of the momentum of the fluid stream. As the urinal screen 100 has limited or no flat surfaces, shoulders, and/or the like, any splashed portion of the fluid stream may be directed such that the splashed portion of the fluid stream further interacts with the urinal screen 100, is directed down toward the urinal floor 210, and/or the like. However, a splashed portion of the fluid stream is not directed back toward the user, due to the geometry of the urinal screen 100.

In certain embodiments, as shown in FIG. 2B, the second (e.g., urinal contacting or facing) face of the urinal screen includes an elevational feature 35, along at least a portion of the substantially planar portion 12, that is configured to elevate at least a portion of the web portion 50 off a urinal floor 210. That is, the second face of the urinal screen 100 may be configured to contact the urinal by elevating at least some of the web portion 50 off the floor 210. For example, the outer ring 10, a portion of the web portion 50, or other elevational features 35 may be provided to elevate all or a majority of the web portion 50. In other embodiments, the urinal contacting face of the urinal screen may be configured such that the web portion 50 contacts the urinal.

The elevational feature 35 may have a variety of configurations and designs, some of which are illustrated at FIGS. 2B and 4. In certain embodiments, the elevational feature 35 includes a plurality of posts or ribs 36 projecting from and/or integral with the second face of the web 50 at the substantially planar portion 12. In some embodiments, the posts of the elevational feature 35 may be the same size and/or pattern as the posts 30 on the urine receiving face of the urinal screen. In other embodiments, the posts of the elevational feature 35 may be a different size, geometry and/or pattern than posts 30 on the urine receiving face of the urinal screen. For example, the posts of the elevational feature 35 may include a tubular or otherwise hollow design.

In some embodiments, as shown in FIGS. 2B and 4, the elevational feature 35 includes a plurality of ribs 36 extending from the second face of the web portion. The ribs 36 may have any suitable, size, geometry, orientation, and placement. For example, the undulating ribs 36 of elevational feature 35 may be integral with a portion of web strings 20. In other embodiments, an elevational feature 35 may be formed by a portion of the web portion having an exaggerated width relative to the remaining portion of the web portion.

In certain embodiments, as described herein, the vaulted portion 14 of the web portion 50 defines a concave inner surface 16 that has a plurality of spacer nubs 32 projecting therefrom. The spacer nubs 32 may be effective to prevent contact between the web portion 50 forming the vaulted portion 14 and the insert 40. That is, the spacer nubs 32 may be sized, shaped, and otherwise configured such that they resist collapse under typical use conditions. Thus, in certain embodiments, the spacer nubs 32 are generally less flexible than the posts 30 that may provide splash reduction on the first face of the web portion 50.

For example, the spacer nubs 32 may be generally formed in similar dimensions to the posts 30 described herein. In certain embodiments, each of the spacer nubs has a height of from about 1 mm to about 1 cm, such as from about 4 mm to about 6 mm, or about 5 mm. In some embodiments, the spacer nubs 32 may have blunt or otherwise non-rounded tips configured to engage the top surface of the insert to provide the desired separation between the insert 40 and the web strings 20. Such separation has been found to provide a suitable drainage path for liquid, such that pooling of liquid in recesses of the urinal screen is substantially reduced.

In certain embodiments, the urinal screen 100 is configured to reduce splashing of a fluid stream incident thereon by providing a reduced area of surfaces that are substantially flat to the user's view (i.e., in plan view) such that any fluid droplets that may splash off of the urinal screen 100 are not directed back toward the user. In particular, it has been discovered that splash back may be reduced by providing a urine receiving face of the urinal screen that has a reduced amount of flat surfaces for an impinging stream of urine to contact. In some embodiments, any combination of the outer ring, each of the plurality of web strings, the exposed block body or shell of an insert, and/or each of the plurality of posts has a generally rounded profile, so as to reduce flat surfaces upon which a stream of urine may be incident.

For example, as compared to current commercial urinal screen offerings, the urinal screens of the present disclosure largely eliminate surfaces that a stream of urine would contact at a roughly 90 degree angle, relative to the pertinent surface. Most commercial urinal screens include a flat section with features protruding to provide splash reduction. In contrast, embodiments of screens of the present disclosure generally do not have a flat base, and instead have a web portion formed by rounded strands intersecting one another. Because of the rounded shape of the strands, such screens have unique geometric characteristics. For example, every imaginary cross-sectional plane taken parallel to the faces of the urinal screen taken across the substantially planar portion of the web portion, yields a semi-unique cross-section. That is, because the thickness of the strands is governed by the equation defining a circle, no cross-section of the substantially planar portion matches more than one other cross-section in a screen having circular web strings forming the web portion. In contrast, similar parallel plane cross-sections in most commercial screens are effectively the same. That is, any cut made between these two planes will match any other cut. This characteristic extends to cuts in the perpendicular plane as well. Because the present screens may have a circular profile, no more than two cross-sections will match because the length of the cross-section again follows the equation of a circle. Thus, such screens may largely eliminate surfaces that a stream of urine would contact at a roughly 90 degree angle and thereby reduce splash.

In various embodiments, the web portion, posts, nubs, tabs, outer rim, and/or elevational features of urinal screen 100 may be molded as a single piece. For example, the urinal screen 100 may be made through injection molding and/or the like. In another embodiment, the urinal screen 100 may be molded from a sheet of polymer material. It should be understood that the urinal screen 100 may be manufactured via a variety of methods known and understood in the art.

The urinal screens 100 disclosed herein may be formed from any suitable materials and combinations of materials known and understood in the art. For example, the urinal screens may be formed of suitable polymer materials. In certain embodiments, any combination of the outer rim, web portion, posts, nubs, tab, and/or elevational feature of the urinal screen 100 may be formed from a matrix material impregnated with an air freshening substance selected from an odor-combatting composition, a fragrance, and a combination thereof. Thus, the air freshening substance may have a scent or be unscented. As used herein, the terms "air freshener" and "air freshening" refer to substances that treat air by combatting or neutralizing odor, providing a fragrance, or both.

The matrix material and air freshening substance may be selected from various suitable materials known in the art. For example, the matrix material may be a polymer, such as ethylene-vinyl acetate (EVA). Suitably, EVA has no odor but can be impregnated with a fragrance or odor-combatting composition. Additionally, EVA approaches elastomeric materials in softness and flexibility, yet can be processed like a thermoplastic. In certain embodiments, the EVA polymer of the cartridge body has a number average molecular weight in the range of about 10,000 Daltons to about 100,000 Daltons, or from about 22,000 to about 87,000 Daltons. Other elastomeric or thermoplastic polymers known in the art may also be used in the cartridge body. For example, the polymer of the cartridge body may include ethyl vinyl alcohol, high density polyethylene, low density polyethylene, polystyrene, acrylic polymers, polycarbonates, polyurethanes, nylons, and mixtures and copolymers thereof.

The matrix material may be impregnated with one or more suitable air freshening substances known in the art. For example, suitable air freshening substances may be selected from those compiled by the U.S. Food and Drug Administration in Title 21 of the Code of Federal Regulations, Sections 172.5 10 and 172.5 15. In certain embodiments, the air freshening substance is selected from the group consisting of benzaldehydes, phenols, cinnamic aldehydes and esters, octadienes, dienes, cyclohexadienes, terpenes, and combinations thereof. In some embodiments, the air freshening substance includes triethylene glycol, a bleach, or hydrogen peroxide. Fragrance oils are also suitable for use alone or in combination with other fragrance chemicals. Suitable fragrance oils include, for examples spice oil, flower oil, and fruit oil. Other suitable fragrances include, but are not limited to, benzyl alcohol, ethyl maltol, furaneol, 1-hexanol, cis-3-hexen-1-ol, menthol, benzaldehyde, hexanal, cinnamaldehyde, citral, cis-3-hexenal, furfural, neral, vanillin, ethyl acetate, ethyl butanoate, ethyl decanoate, ethyl hexanoate, ethyl octanoate, hexyl acetate, isoamyl acetate, methyl butanoate, methyl salicylate, pentyl butanoate, pentyl pentanoate, sotolon, strawberry aldehyde, fructone, anethole, anisole, eugenol, dihydrojasmone, 2-acetyl-1-pyrroline, 6-acetyl-2,3,4,5-tetrahydropyridine, gamma-decalactone, gamma-nonalactone, delta-octalactone, jasmine lactone, massoia lactone, camphor, citronellol, linalool, nerol, nerolidol, alpha-terpineol, thujone, and thymol. In certain embodiments, the air freshening substance may include one or more additives, such as hindered amines or antioxidants.

In certain embodiments, the material forming the urinal screen 100 contains the air freshening substance in an amount of from about 1 percent by weight to about 75 percent by weight of the impregnated matrix material. In some embodiments, the urinal screen contains the air freshening substance in an amount of from about 10 percent by weight to about 50 percent by weight. In some embodiments, the urinal screen contains the air freshening substance in an amount of from about 10 percent by weight to about 20 percent by weight, such as about 15 percent by weight, or about 14.5 percent by weight. In some embodiments, the urinal contains the air freshening substance in an amount of from about 20 percent by weight to about 50 percent by weight. In some embodiments, the urinal screen contains the air freshening substance in an amount of from about 30 percent by weight to about 40 percent by weight. In one embodiment, the urinal screen contains the air freshening substance in an amount of about 25 percent by weight. In one embodiment, the urinal screen contains the air freshening substance in an amount of about 35 percent by weight. The ratio of air freshening substance to matrix material in the urinal screen may be selected to provide the desired release of the air freshening substance.

In certain embodiments, the material forming the urinal screen may contain the air freshening substance in an amount that is lower than in traditional screens, such as from about 15 percent or less, such as from about 0.1 percent to about 10 percent, by weight of the impregnated matrix material. For example, utilization of a bioenzymatic block in combination with a urinal screen containing an air freshening substance may reduce the amount of air freshening needed due to the effect of the odor combatting chemistry of the enzyme block in reducing drain buildup and improving odor without masking it with fragrance. That is, use of the bioenzymatic blocks discussed herein may facilitate reduction of the odor without the use of air freshening fragrance substances.

In certain embodiments, as shown in FIGS. 3A-3F, urinal screen assemblies 300 are provided that include any embodiment of a urinal screen 100 (e.g., web portion, outer ring, posts, and/or nubs) in combination with an insert 40 having a chemistry containing (e.g., odor-combatting, bioenzymatic) block 42. For example, the insert 40 may be disposed in a void formed by the vaulted portion 14 of the web portion 50. As discussed above, in certain embodiments, the spacer nubs 32 are effective to space the insert 40 from the web portion 50, which advantageously may help mitigate or eliminate trapping of fluid between the insert 40 and the web portion 50.

Thus, urinal screens that are functional to screen debris and provide drainage while also reducing the splash of urine during use, as compared to commercially available screens and urinals without screens, and optionally with air freshening characteristics and/or other odor combatting chemistry inserts, have been developed. Such urinal screens advantageously reduce the splashing of the fluid stream incident thereon by presenting a reduced area of surfaces that are substantially flat to the user's view and/or by providing posts having a size and geometry selected to absorb some of the momentum of a splashed fluid stream and redirect the fluid back toward the urinal floor. Such urinal screens thereby solve the problems of splash common in known urinal screens that lack splash reducing features and urinal screens containing surfaces that are substantially flat to the user's view. Furthermore, these urinal screen assemblies may beneficially provide reduced splashing in combination with the odor combatting or other effects of the insert and its chemistry-containing block. Moreover, these urinal screens may reduce or eliminate pooling of liquid within the urinal screen.

While the disclosure has been described with reference to a number of example embodiments, it will be understood by those skilled in the art that the invention is not limited to such embodiments. Rather, the invention can be modified to incorporate any number of variations, alterations, substitutions, or equivalent arrangements not described herein, but which are commensurate with the spirit and scope of the invention. Additionally, while various example embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A urinal screen, comprising:
    an outer ring;
    a web portion bounded by the outer ring and having a first face and an opposed second face, the web portion comprising a plurality of web strings disposed in a mesh pattern, such that a plurality of open areas are defined among the web strings; and
    a plurality of posts projecting from the first face of the web portion,
    wherein the web portion comprises a planar portion and a vaulted portion, with the planar portion extending from the outer ring and surrounding the vaulted portion, and
    wherein portions of the web strings forming the first face of the web portion are substantially rounded in profile, each of the plurality of posts comprises a substantially rounded tip and a substantially rounded profile, and the vaulted portion has a rounded profile, such that the portions of the web strings forming the first face, the plurality of posts, and the vaulted portion are each effective to reduce splash back of liquid impinging thereon.

2. The urinal screen of claim 1, wherein the planar portion and the vaulted portion are integrally formed.

3. The urinal screen of claim 1, wherein the vaulted portion comprises a hemisphere or dome.

4. The urinal screen of claim 1, wherein the open areas of the web portion have a major dimension of from about 1 mm to about 30 mm in plan view.

5. The urinal screen of claim 1, wherein each of the plurality of posts has a height of from about 0.5 mm to 1 cm.

6. The urinal screen of claim 1, wherein the plurality of web strings comprise a first set of the web strings that are substantially parallel to one another and a second set of the web strings that are substantially parallel to one another and are substantially perpendicular to the first set of web strings.

7. The urinal screen of claim 1, wherein the second face comprises an elevational feature configured to elevate at least a portion of the web portion off of a urinal floor, the elevational feature comprising a plurality of posts or ribs projecting from and/or integral with the second face of the web portion.

8. A urinal screen assembly, comprising:
    the urinal screen of claim 1; and
    a bioenzymatic block containing odor combatting chemistry disposed in a void formed by the vaulted portion.

9. The urinal screen assembly of claim 8, further comprising a plurality of spacer nubs projecting from an inner surface of the vaulted portion, wherein the spacer nubs are effective to space the bioenzymatic block from the web portion.

10. The urinal screen assembly of claim 8, further comprising a cover surrounding the bioenzymatic block.

11. The urinal screen assembly of claim 10, wherein the cover comprises a waterproof upper surface covering an upper surface of the bioenzymatic block to protect the bioenzymatic block from liquids impinging thereon, and a base covering a lower surface of the bioenzymatic block and comprising at least one aperture to permit liquid to contact the bioenzymatic block at its lower surface and thereby release the odor combatting chemistry.

12. The urinal screen of claim 1, wherein the plurality of posts are positioned at nodes at which two web strings intersect, at midpoints between adjacent pairs of nodes, or both.

13. A urinal screen, comprising:
    an outer ring;
    a web portion bounded by the outer ring and having a first face and an opposed second face, the web portion comprising a plurality of web strings disposed in a mesh pattern, such that a plurality of open areas are defined between the web strings, wherein the web portion comprises a vaulted portion defining a concave inner surface; and
    an article disposed in the void formed by the vaulted portion, the article comprising a block containing odor combatting chemistry and having an upper surface,
    wherein a plurality of spacer nubs project from the concave inner surface of the vaulted portion, the spacer nubs being configured to space the web portion from the upper surface of the article.

14. The urinal screen of claim 13, wherein the web portion comprises a planar portion and a vaulted portion, with the planar portion extending from the outer ring and surrounding the vaulted portion.

15. The urinal screen of claim 14, wherein the planar portion and the vaulted portion are integrally formed.

16. The urinal screen of claim 13, wherein the vaulted portion comprises a hemisphere, a dome, a frustocone, or a cylinder.

17. The urinal screen of claim 13, wherein portions of the web strings forming the first face of the web portion are substantially rounded in profile.

18. The urinal screen of claim 13, wherein the plurality of web strings comprise a first set of the web strings that are substantially parallel to one another and a second set of the web strings that are substantially parallel to one another and are substantially perpendicular to the first set of web strings.

19. The urinal screen of claim 13, wherein the second face comprises an elevational feature configured to elevate at least a portion of the web portion off of a urinal floor, the elevational feature comprising a plurality of posts or ribs projecting from or integral with the second face of the web portion.

20. The urinal screen of claim 13, wherein each of the spacer nubs has a height of from about 1 mm to about 1 cm.

21. The urinal screen of claim 13, wherein the block is a bioenzymatic block containing odor combatting chemistry.

22. The urinal screen of claim 13, wherein the article further comprises a cover surrounding the block, the cover defining the upper surface of the article.

* * * * *